(12) United States Patent
Boy et al.

(10) Patent No.: US 8,293,504 B2
(45) Date of Patent: Oct. 23, 2012

(54) METHOD FOR THE PRODUCTION OF AN AQUEOUS GLUCOSE SOLUTION

(75) Inventors: Matthias Boy, Bensheim (DE); Jong-Kyu Choi, Jeonju (KR); Jin Won Chung, Gunsan (KR); Markus Lohscheidt, Heidelberg (DE); Jong In Choi, Gunsan (KR); Jae Yeol Seo, Jeonju (KR); Jörg Braun, Essingen (DE); Mo Se Kim, Jeonju (KR); Sung Hyun Kim, Jeonbuk (KR); Arno Kochner, Waldsee (DE)

(73) Assignee: BASF SE (DE)

( * ) Notice: Subject to any disclaimer, the term of this patent is extended or adjusted under 35 U.S.C. 154(b) by 495 days.

(21) Appl. No.: 12/667,717

(22) PCT Filed: Jul. 4, 2008

(86) PCT No.: PCT/EP2008/058709
§ 371 (c)(1),
(2), (4) Date: Jan. 5, 2010

(87) PCT Pub. No.: WO2009/007326
PCT Pub. Date: Jan. 15, 2009

(65) Prior Publication Data
US 2010/0196964 A1 Aug. 5, 2010

(30) Foreign Application Priority Data
Jul. 6, 2007 (EP) .................................... 07111976

(51) Int. Cl.
| | |
|---|---|
| C12P 19/02 | (2006.01) |
| C12P 19/12 | (2006.01) |
| C12P 19/00 | (2006.01) |
| C12P 19/30 | (2006.01) |
| C12P 1/00 | (2006.01) |
| C12P 13/00 | (2006.01) |
| C12P 7/42 | (2006.01) |
| C09K 3/00 | (2006.01) |
| A61K 36/00 | (2006.01) |
| A23K 3/00 | (2006.01) |

(52) U.S. Cl. ............. 435/105; 435/41; 435/72; 435/89; 435/100; 435/128; 435/146; 435/148; 435/158; 252/182.12; 530/370

(58) Field of Classification Search .................... 435/41, 435/72, 89, 100, 105, 128, 146, 148, 158; 252/182.1; 530/370
See application file for complete search history.

(56) References Cited

U.S. PATENT DOCUMENTS

| 4,287,304 A | 9/1981 | Muller et al. |
|---|---|---|
| 4,361,651 A | 11/1982 | Keim |
| 4,448,881 A | 5/1984 | Muller et al. |
| 2005/0233030 A1 | 10/2005 | Lewis et al. |
| 2005/0239181 A1 | 10/2005 | Lewis et al. |
| 2008/0254515 A1 | 10/2008 | Boy et al. |
| 2008/0299606 A1 | 12/2008 | Pompejus et al. |
| 2008/0318287 A1 | 12/2008 | Boy et al. |
| 2009/0162892 A1 | 6/2009 | Pompejus et al. |
| 2009/0226571 A1 | 9/2009 | Freyer et al. |
| 2009/0317515 A1 | 12/2009 | Lohscheidt et al. |

FOREIGN PATENT DOCUMENTS

| CN | 1173541 A | 2/1998 |
|---|---|---|
| CN | 1067433 C | 6/2001 |
| WO | WO-2005/116228 A2 | 12/2005 |
| WO | WO-2006/004748 A2 | 1/2006 |
| WO | WO-2007/028804 A1 | 3/2007 |
| WO | WO-2009/007326 A2 | 1/2009 |

OTHER PUBLICATIONS

McAloon, A., et al., "Determining the Cost of Producing Ethanol from Corn Starch and Lignocellulosic Feedstocks", NREL/TP-580-28893, (2000), 43 pages.
Jakel, N., "Higher Value Coproducts", Biofuels Journal, (2006), 2 pages.
Guo, X., et al., "Study of Maize Gluten Extraction Technology", Cereals and Oils Processing, vol. 2, (2007), pp. 53-55.

*Primary Examiner* — Herbert J Lilling
(74) *Attorney, Agent, or Firm* — Connolly Bove Lodge & Hutz LLP

(57) ABSTRACT

The present invention relates to a process for the production of an aqueous glucose solution from maize or maize kernels. The invention also relates to a glucose solution obtainable by this process, and to its use for the production of organic compounds. The process according to the invention comprises: a) fractionating dry milling of maize kernels, where the maize kernels are separated into a maize-starch-comprising endosperm fraction and a high-oil germ fraction and, if appropriate, a bran fraction; b) enzymatic liquefaction and saccharification of the maize starch in an aqueous suspension of the endosperm fraction, which gives an aqueous glucose solution comprising maize gluten; and c) depletion of the maize gluten and, if appropriate, any bran present from the aqueous glucose solution.

8 Claims, No Drawings

METHOD FOR THE PRODUCTION OF AN AQUEOUS GLUCOSE SOLUTION

RELATED APPLICATIONS

This application is a national stage application (under 35 U.S.C. §371) of PCT/EP2008/058709, filed Jul. 4, 2008, which claims benefit of European application 07111976.2, filed Jul. 6, 2007.

The present invention relates to a process for the production of an aqueous glucose solution from maize or maize kernels. The invention also relates to a glucose solution obtainable by this process, and to its use for the production of organic compounds.

Glucose, in particular aqueous glucose solutions, is a basic carbon source for many chemical and fermentative processes for the preparation of organic products. By way of example, the fermentation involves the metabolization of the glucose molecules by the microorganisms employed, whereby they are converted into the desired organic product of interest. The range of organic products thus prepared comprises, for example, low-molecular-weight volatile compounds such as ethanol, aliphatic carboxylic acids, amino acids, vitamins, carotenoids, sugar alcohols, sugar acids and polyols, but also enzymes and organic polymers.

Such generally known fermentation processes utilize different carbon sources, depending on the process conditions and the products to be produced. These carbon sources range from pure sucrose via sugarbeet molasses and sugarcane molasses, glucose from starch hydrolyzates to glycerol.

In the conventional production of glucose from starch, the starch is first obtained from a natural starch source such as potatoes, cassava, cereals, for example wheat, maize, barley, rye, triticale or rice, and subsequently hydrolyzed, generally by enzymatic liquefaction, followed by enzymatic saccharification.

In the production of glucose by liquefying and saccharifying starch, the starting material is, as a rule, a prepurified starch, i.e. the natural starch sources such as potatoes, cassava and cereals, for example wheat, maize, barley, rye, triticale or rice, are separated into starch constituents and nonstarch constituents.

In cereals, in particular in the case of maize, the prepurified starch is obtained by a multistep wet-milling procedure. To this end, the cereal kernels are first swollen in water. In a second step, the swollen kernels are comminuted with addition of water, whereupon the germ is removed. After removal of the germ, the remaining constituents, i.e. starch, gluten and bran (fiber constituents) are subjected to a fine-milling process. In further steps, the bran and the gluten are removed, so that, in the end, an aqueous starch suspension is obtained which is subsequently subjected to a liquefaction/saccharification step in order to produce glucose. Very pure glucose is obtained in this manner.

The wet-milling of cereal kernels, however, is relatively complicated. Since the cereal kernels are first dipped in water, the secondary products and waste products which are generated in the production of starch, such as proteins (gluten), germ constituents and fiber constituents, must be dried before further processing or disposal, which entails a considerable expenditure of energy. In addition, the equipment is complex, and corresponding plants therefore require a great capital outlay. On the other hand, since cereals and in particular maize are important starch sources, there has been no lack of attempt to provide more advantageous alternatives for obtaining glucose from these starch sources.

A more economic method of utilizing the starch constituents of cereals, in particular maize, is dry milling of the cereal kernels. To this end, the cereal kernels, if appropriate after having been moistened with small amounts of water for improving the germ's smoothness, are milled, and the milled stock obtained is subjected, as a whole, to an enzymatic liquefaction/saccharification step. In this manner, an aqueous glucose is obtained which comprises large amounts of insoluble solids resulting from the cereal's nonstarch constituents, viz. fibers from the husks, oil from the germs and proteins, i.e. gluten. Processes for the preparation of glucose by dry milling cereals followed by liquefaction/saccharification are known and described, for example, in "The Alcohol Textbook—A reference for the beverage, fuel and industrial alcohol industries", Jaques et al. (ed.), Nottingham Univ. Press 1995, ISBN 1-8977676-735, chapter 2, pp. 7 to 23, and in McAloon et al., "Determining the cost of producing ethanol from corn starch and lignocellulosic feedstocks", NREL/TP-580-28893, National Renewable Energy Laboratory, October 2000.

The glucose which has been obtained by dry-milling processes has, on an industrial scale, hitherto only been used for the production of bioethanol. The reason therefor are several disadvantages which are inherent to this process: firstly, the consequence of the high percentage of nonsoluble constituents in the aqueous glucose thus produced is that the viscosity of the aqueous glucose solution is high, even at low glucose concentrations, and, moreover, the aqueous glucose solution is shear thinning. As a consequence, the maximum glucose concentration in an aqueous glucose thus produced is limited to, as a rule, 30 to 33% by weight. While high glucose concentrations are not necessary, or, owing to the toxicity of the ethanol formed during the fermentation, even problematic for the fermentative bioethanol production, a low glucose concentration leads to an undesirable increase in the volume flow in the production of other chemicals. Moreover, the nonsoluble constituents may have a negative effect on the fermentation, for example with regard to the oxygen transfer rate or the oxygen requirements of the microorganisms employed for the fermentation. Moreover, these solids may have a not inconsiderable negative effect on the subsequent processing and isolation of the product obtained by fermentation. In the production of bioethanol by anaerobic fermentation followed by separation by distillation, these problems only play a minor role.

In recent years there have been various reports on the use of a glucose, produced by a dry-milling process, in the fermentative production of fine chemicals (see WO 2005/116228 and WO 2007/028804). The process of dry milling with subsequent liquefaction/saccharification which has been described in these applications permits the production of an aqueous glucose with an increased sugar concentration without it being necessary to separate the insoluble solids present in the starch source. In some cases, however, the use of a glucose produced in this manner leads to an inhibition, or delayed multiplication, of the microorganisms.

As has already been illustrated above, the aqueous glucose produced by a dry-milling process with subsequent liquefaction/saccharification comprises not only the fermentable sugar constituents, but also large amounts of insoluble solids which cannot be fermented. When employing such an aqueous glucose in a fermentation, be it for the production of bioethanol or for the production of fine chemicals, these solids are passed through the fermentation process and thus increase the volume flow. After the fermentation product has been separated off, they remain as a solid which must be disposed of or which, at best, may be used as animal feed.

Since some of the constituents which cannot be fermented are, however, products of value themselves, it has been reported by various authors to separate off some or all of these constituents before the fermentation.

In the context of the bioethanol production, for example, US 2005/0233030 and US 2005/0239181 and N. Jakel in Biofuels Journal (http://www.renessen.com/news_release/Renessen_ethanol_art.pdf) describe the dry milling of maize, where the milled stock is separated into a high-starch endosperm fraction and a low-starch germ/fiber fraction and essentially only the endosperm fraction is subjected to a liquefaction/saccharification step. In this manner, the amount of the coproduct generated in the fermentative production of ethanol may be reduced. Moreover, the germ/fiber fraction may be used for the production of vegetable oil.

U.S. Pat. No. 4,287,304 describes a process for the production of an aqueous glucose solution from dry-milled maize. In this process, the dry-milling process first generates a germ/fiber fraction and a high-starch endosperm fraction which, besides the starch, still comprises protein constituents (gluten) and part of the oil present in the kernels. The endosperm fraction is subsequently subjected to a liquefaction process. The insoluble constituents, i.e. protein and oil constituents, are separated from the resulting aqueous starch partial hydrolyzate. Thereafter, the liquefied starch, that is to say the aqueous starch partial hydrolyzate, is subjected to a saccharification process. Some of the Applicant's studies have demonstrated that the separation of the insoluble constituents at the liquefied starch stage is problematic and complicated and entails glucose losses. Moreover, an aqueous glucose with a comparably low glucose concentration is obtained in this manner.

CN 1173541 describes a process for the production of lactic acid by fermentation, where a glucose obtained from maize or rice is employed as the sugar source. In the process described in that publication, maize or rice are subjected to dry milling, and the milled stock obtained is first subjected to a liquefaction process. The slurry obtained in this process is separated into a liquid phase which comprises the partially hydrolyzed starch constituents and a solid phase which comprises the insoluble solid constituents of the milled stock which cannot be fermented. The liquid phase is subsequently subjected to a saccharification process. This process has similar disadvantages as the process described in U.S. Pat. No. 4,287,304. The separation, before the fermentation process, of the solid constituents which cannot be fermented is performed to allow them to be used as feedstuff.

Accordingly, the object of the present invention is to provide a process for the production of an aqueous glucose from maize which does not have the disadvantages of the prior art. In particular, it is intended that the glucose obtained in the process is suitable not only for the production of bioethanol, but also for the production of other fine chemicals.

This and further objects are achieved by the process described hereinbelow. Accordingly, the present invention relates to a process for the production of an aqueous glucose solution from maize, comprising the following steps:

a) Fractionating dry-milling of maize kernels, where the maize kernels are separated into a maize-starch-comprising endosperm fraction and a high-oil germ fraction and, optionally, a bran fraction;
b) Enzymatic liquefaction and saccharification of the maize starch in an aqueous suspension of the endosperm fraction, which gives an aqueous glucose solution comprising maize gluten; and
c) Depletion of the maize gluten and, optionally, any bran present from the aqueous glucose solution.

The process according to the invention entails a series of advantages. Firstly, the equipment for the production of an aqueous glucose solution by the process according to the invention is much less complicated than in the conventional wet-milling process, and much less energy is required for the production of an aqueous glucose solution by the process according to the invention than in the conventional wet-milling process. Secondly, the glucose obtainable by the process according to the invention is particularly suitable as carbon source for fermentative processes for the production of chemicals. Not only is it markedly better suited than a glucose solution which is obtainable by liquefaction/saccharification of a maize flour produced by dry milling, but it also leads, in the case of a series of microorganisms, to a better growth of the microorganisms employed for the fermentation and/or to higher yields, based on the glucose employed, in comparison with pure glucose, or a glucose obtained in a wet-milling process. Thirdly, the process according to the invention permits the production of glucose solutions with a high glucose concentration. The viscosity properties of a glucose obtainable in accordance with the invention are markedly superior to those of a glucose which has been produced by liquefaction/saccharification of a maize flour produced by conventional dry milling without fractionation.

The terms "bran" or "coat" are to be understood as meaning the hard external shell of the maize kernel, the pericarp (as a rule <2% by weight of the maize kernel). "Bran constituents", or "coat constituents", are fragments or parts of the above. The "bran fraction" or "coat fraction" consists mostly of the bran or the coat, but may also comprise other constituents of the maize kernel, in particular parts of the endosperm.

The term "germ" is understood as meaning the embryo of the maize kernel (as a rule 8 to 10% by weight of the maize kernel). "Germ constituents" are fractions or parts thereof. The "germ fraction" consists mostly of the germ, but may also comprise other constituents of the maize kernel, for example parts of the endosperm or of the bran.

The term "endosperm" is understood as meaning the primarily starch-comprising part of the maize kernel (as a rule 80 to 85% by weight of the maize kernel). The "endosperm fraction" consists mostly of the endosperm, but may also comprise other constituents, for example parts of the germ or of the bran.

The glucose solutions produced by the process according to the invention have a characteristic composition which is absent in glucose solutions produced via other routes. They are therefore novel and likewise subject matter of the present invention.

Moreover, the protein constituent maize gluten, which is generated in step c) of the process according to the invention, is distinguished by a specific quality which distinguishes it from the gluten constituents generated in other maize-processing processes and which makes it suitable for many applications. Accordingly, the present invention also relates to the maize gluten generated in step c).

Step a):

In step a) of the process according to the invention, maize kernels are subjected to fractionating dry-milling. The fractionating milling serves to comminute the maize kernels and to separate the maize kernel into its constituents, which are germ, endosperm and coat constituents (hereinbelow also termed bran constituents).

In accordance with the invention, most, i.e. at least 70% by weight, in particular at least 80% by weight, of the germs or germ constituents present in the maize kernels are separated at this stage from the remaining constituents of the maize kernel, i.e. endosperm and coat constituents, to form a high-oil germ fraction. As a rule, the fractionating dry milling step also results in a separation into an endosperm fraction, which comprises essentially the starch and protein constituents of the maize kernels, and into a bran fraction, which comprises essentially, i.e. at least 60% by weight, in particular at least 80% by weight, of the coat constituents present in the maize kernels.

However, some or all, for example 10 to 100% by weight, of the bran fraction may be subjected to the liquefaction and saccharification in step b) together with the endosperm fraction, in order to avoid starch losses. Alternatively, it is possible to put the bran fraction to different use and only to subject the endosperm fraction and, if appropriate, small amounts of bran, i.e. less than 20% by weight based on the bran constituents present in the maize kernels, to the liquefaction/saccharification in step b).

The maize kernels may be employed as delivered when subjecting the maize kernels to the fractionating dry-milling process. Preferably, however, one will employ cleaned maize kernels. The cleaning process removes not only coarsely-particulate impurities, for example woodchips, plant constituents such as stems or leaves, stones, broken glass, screws and the like, but also finely-particulate impurity such as broken maize kernels, other seeds, pebbles, and sand from the maize kernels. The removal can be effected in a manner known per se, for example by screening, sifting or combinations of these measures. As a rule, a procedure will be followed in which coarsely-particulate particles are first removed from the maize kernels and the finely-particulate impurities, and the finely-particulate particles will then be removed from the maize kernels. Coarsely-particulate particles are considered those whose particle size is at least above a limit of 15 to 20 mm. Finely-particulate particles are considered those particles whose maximum particle size does not exceed a value of from 5 to 6.5 mm.

Since the finely-particulate impurities comprise not only sand and dust components, but also broken maize kernels, it is advantageous to subject the finely-particulate impurities to another fractionation. To this end, the finely-particulate impurities are separated into a first fraction with a maximum particle size of from 3.5 to 4.5 mm, which comprises essentially sand and other dust-like material, and a slightly more coarsely-particulate fraction with particle sizes of at least 3.5 to 4.5 mm, which comprises essentially small or broken maize kernels. The last-mentioned fraction can be returned to the cleaned maize in order to reduce starch losses. The first fraction can be added to the bran fraction resulting from the fractionation.

The maize which has been cleaned thus is subsequently subjected to the fractionating dry-milling process. The fractionating milling process is carried out in a manner known per se. As a rule, the dry-milling process is divided into a first milling stage, where the germ is removed, or a separation into an endosperm fraction, a germ fraction and a bran fraction is performed, and a second milling stage, where the endosperm fraction is milled to the desired particle size. It is clear to the skilled worker that the separation will, as a rule, not be complete, but is only carried out until the desired purity of the fractions has been reached, i.e. once the germ has been separated off, the endosperm fraction will, as a rule, still comprise up to 30% by weight, preferably no more than 20% by weight, of the germ constituents present in the maize kernel, and, once the bran constituents have been separated off, up to 40% by weight, preferably no more than 20% by weight, of the coat constituents present in the maize kernel.

In the first stage, frequently also termed maize degerming, the maize kernels are comminuted, for example by cylinder mills as are obtainable for example from Bühler AG or Ocrim spa, by special degerminators, for example devices with one or more roller-type rotors which are surrounded by a structured screen, or else by a combination of these apparatuses. The process may be carried out as a one-step operation and is preferably carried out in several milling steps. After a milling operation, the milled stock is separated in a manner known per se to give an endosperm fraction, a germ fraction and a bran fraction. Here, a procedure will, as a rule, be followed in which a separation into an endosperm fraction and into a bran and germ fraction is first performed, and the bran and germ fraction which has been removed is separated, in a second step, into its constituents. Since, as a rule, the endosperm constituents of the milled stock will have smaller particle sizes than the particles of the germ and bran fraction of the milled stock, the first separation may be performed in a simple manner by a screening method. The separation of the germ and bran fraction of the milled stock may be carried out for example by sifting. Naturally, the individual separation steps may comprise combinations of these measures.

In a multi-step maize degerming process, the endosperm fraction of a preceding stage is, in a downstream stage, comminuted further and processed analogously to the above-described procedure. 2- to 4-stage processes are typical. The plurality of stages leads to higher purities of the individual fractions and to a higher starch yield of the endosperm fraction.

When using degerminators, particularly small particles may be generated in the first stage, and these particles are no longer capable of being separated into the three desired fractions endosperm, germ and bran by means of screening or sifting. These particles are, as a rule, added to the bran fraction, where it may be advantageous, in order to achieve a high starch yield, to add these particles to the endosperm fraction before or during the fine-milling process.

It has proven advantageous for the maize degerming process for the maize to have a certain moisture content, which is in the range of from 5 to 30% by weight and in particular in the range of from 12 to 20% by weight. Accordingly, maize which does not have the desired moisture content will be treated with a small amount of water before or during the maize degerming process. After the addition of water, the maize is preferably stored over a period of from 0.5 to 24 h before being processed further, whereby the moisture which adheres to the surface can penetrate into the inside of the maize kernel, specifically to the maize germ. As a rule, the milling process in step a) is therefore carried out in the presence of from 5 to 30% by weight of water, based on the weight of the maize kernels employed. Preferably, the amount of water is 10 to 25% by weight, and in particular 12 to 20% by weight. The water is preferably added before the maize degerming process but it may also be added during the maize degerming process. In a multi-step degerming process, the water content may be readjusted between the respective degerming steps. If appropriate, the water may also be added in the form of steam. The skilled worker can readily determine the water content by analyzing the maize kernels employed, but also the milled stock obtained in the respective stage, and can readily identify required amounts of additional water.

As a rule, this is followed by at least one further milling of the endosperm fraction, which may likewise consist of one or more milling steps. Here, the endosperm fraction is brought to the particle size which is most advantageous for the liquefaction/saccharification process. This step is frequently also referred to as fine milling. During the fine-milling process, the endosperm fraction is, as a rule, milled to a mean particle diameter in the range of from 0.05 to 1.5 mm and preferably to a particle size in the range of from 0.1 to 1 mm and specifically in the range of from 0.25 to 0.8 mm. The mean particle diameter is mass-based and is determined in a manner with which the skilled worker is familiar, preferably by means of screen analysis. In particular, it has proved advantageous when at least 80% by weight, in particular at least 90% by weight and specifically at least 95% by weight of the particles have a diameter of no more than 0.4 mm. When the fine-milling process is carried out in a plurality of steps, each milling process is preferably followed by a separation into particles whose size is above the desired maximum size and particles whose size does not exceed the desired maximum level. Only the unduly large particles are then subjected to a further milling process.

As has already been illustrated above, some or all of the bran fraction may be returned to the endosperm fraction in order to avoid starch losses. This is preferably done before or during the fine-milling process. Preferably, however, the bran fraction is not returned to the endosperm fraction.

The fractions which have been separated thus typically have the following compositions:

The bran constituent typically comprises the following constituents in the following amounts (based on the total dry matter):

Crude protein: 1 to 20% by weight, preferably 5 to 15% by weight
Starch: 1 to 30% by weight, preferably 5 to 20% by weight
Crude fiber: 1 to 40% by weight, preferably 5 to 20% by weight
Crude fat: 0 to 20% by weight, preferably 0.5 to 15% by weight
Crude ash: 0 to 10% by weight, preferably 0.1 to 5% by weight The moisture content of the bran is typically between 8 and 20% by weight, preferably between 10 and 17% by weight.

The maize bran is a husk-like material consisting of predominantly thin particles. The mean diameter of these thin particles is between 0.5 mm and 8 mm, preferably between 0.6 mm and 5 mm. The mean height of the thin particles is between 0.01 mm and 4 mm, preferably between 0.05 mm and 2 mm.

The germ fraction typically comprises the following constituents in the following amounts (based on the total dry matter):

Crude protein: 1 to 30% by weight, preferably 5 to 20% by weight
Starch: 1 to 60% by weight, preferably 5 to 50% by weight
Crude fiber: 1 to 20% by weight, preferably 2 to 12% by weight
Crude fat: 8 to 40% by weight, preferably 10 to 35% by weight
Crude ash: 0 to 15% by weight, preferably 0.1 to 10% by weight The moisture content of the maize germ is typically between 8 and 20% by weight, preferably between 10 and 15% by weight.

The maize germ is somewhat drop-shaped. The mean diameter of these particles is between 0.1 mm and 5 mm, preferably between 1 mm and 4 mm. The mean height of the particles is between 2 mm and 10 mm, preferably between 3 mm and 8 mm.

The endosperm fraction typically comprises the following constituents in the following amounts (based on the total dry matter):

Crude protein: 1 to 30% by weight, preferably 5 to 15% by weight
Starch: 40 to 95% by weight, preferably 60 to 90% by weight
Crude fiber: 0 to 20% by weight, preferably 0.2 to 12% by weight
Crude fat: 0.2 to 10% by weight, preferably 0.5 to 5% by weight
Crude ash: 0 to 15% by weight, preferably 0.1 to 3% by weight The moisture content of the endosperm is typically between 8 and 20% by weight, preferably between 8 and 15% by weight.

As regards the germ, the bran and the endosperm fraction, only those constituents which are relevant to feedstuffs are given, as they are obtained in a typical analysis. The value given for crude protein comprises the total Kjeldahl nitrogen multiplied by the factor 6.25, that is to say not only proteins, but for example also further free amino acids, nucleic acids and inorganic nitrogen. The value given for crude fiber comprises, as its main constituent, cellulose and hemicelluloses, but encrusting substances such as lignin are also recorded. The value for crude fat includes all substances which, such as, for example, triglycerides, free fatty acids and phospholipids, dissolve in fat solvents such as, for example, petroleum ether or hexane. The crude ash comprises all inorganic constituents which remain after heating at 550° C. over a prolonged period. These are essentially minerals in the form of oxides and salts. Besides the starch which is analyzed separately, nonstarch polysaccharides such as, for example, pentosans, are not identified in the chosen analysis, or only inaccurately.

The terms used in this context, crude protein, crude fiber constituents, crude fat and crude ash, are known to the skilled worker and defined for example in Naumann, C., Bassler, R., 1976. VDLUFA-Methodenbuch, volume 3, Die chemische Untersuchung von Futtermitteln [Chemical Analysis of Feedstuffs] (Loose-leaf edition with supplements from 1983, 1988, 1993, 1997 and 2004), VDLUFA-Verlag, Darmstadt, Germany [Compilation of all parameters/methods which are relevant for the assessment of feedstuffs in Germany].

Step b)

The maize flour thus obtained, which comprises essentially the endosperm fraction and, if appropriate, the bran fraction, is then subjected to an enzymatic liquefaction and saccharification process, during which process the starch constituents of the endosperm fraction are hydrolyzed to give glucose. In a first step b.1), the maize flour obtained in step a) is liquefied, during which process the starch constituents of the maize flour are typically digested or hydrolyzed to give sugar chains with 4 to 20 and in particular 8 to 12 glucose units. This step is hereinbelow also referred to as liquefaction.

The liquefaction can be carried out in the customary manner by addition of enzymes. Processes for doing so are known from the prior art cited at the outset, for example from "The Alcohol Textbook—A reference for the beverage, fuel and industrial alcohol industries", Chapter 2, pages 7 to 23, which has been cited at the outset.

To this end, the maize flour obtained in step a) will first be mixed with an aqueous fluid, for example fresh water, recirculated process water, for example from subsequent fermentation or evaporation, or with a mixture of these fluids, an aqueous suspension being obtained. This procedure is frequently also referred to as slurrying.

The amount of flour is chosen in such a way that the suspension comprises 25 to 50% by weight, preferably 30 to 45% by weight and very especially preferably 32 to 38% by weight of starch, based on the total weight of the suspension (slurry). Since, as a rule, 1 kg of starch yields 1.0 to 1.1 kg of mono-, di- and oligosaccharides in a liquefaction/saccharification process, the total concentration of mono-, di- and/or oligosaccharides in the glucose obtained after the saccharification is, accordingly, in the range of from 250 to 550 g/kg, preferably in the range of from 300 to 495 g/kg and in particular in the range of from 320 to 410 g/kg. Here, glucose generally accounts for at least 80% by weight, in particular for at least 90% by weight, based on the total amount of mono-, di- and/or oligosaccharides.

As a rule, the temperature of the water employed is chosen in such a way that the suspension has a temperature in the range of from 30 to 60° C., preferably 40 to 58° C. and very especially preferably 50 to 55° C. A temperature of 60° C. should preferably not be exceeded in order to prevent undesirable gelatinization of the starch.

In principle, all starch-liquefying enzymes may be employed for liquefying the starch component in the maize flour, in particular α-amylases (enzyme class EC 3.2.1.1), for example α-amylases which are obtainable from *Bacillus lichenformis* or *Bacillus staerothermophilus*, inter alia those which are employed for liquefying substances obtained by dry-milling processes in connection with the production of bioethanol. The α-amylases which are suitable for the liquefaction are also commercially available, for example from Novozymes under the name Termamyl 120 L, type L; or from Genencor under the name Spezyme. A combination of different α-amylases may also be employed for the liquefaction. The enzyme concentration in the slurry based on the starch content is, as a vile, 0.01 to 0.2% by weight, especially preferably 0.02 to 0.1% by weight and very especially preferably 0.04 to 0.08% by weight.

Advantageously, the amounts of starch-liquefying enzyme and maize flour will be chosen in such a way that the viscosity during the gelling process is sufficiently reduced to make possible the efficient mixing of the suspension, for example by means of stirring. Preferably, the viscosity of the reaction mixture during gelling is not more than 20 Pas, especially preferably not more than 15 Pas and very especially preferably not more than 8 Pas. As a rule, the viscosity is measured with a Haake viscometer, type Roto Visko RV20 with M5 measuring system and MVDIN measuring device at a temperature of 50° C. and a shear rate of 200 $s^{-1}$.

The liquefaction is frequently carried out in the presence of at least one calcium salt. In this case, the calcium concentration in the slurry will be adjusted to, as a rule, 10 to 200 ppm, preferably 15 to 100 ppm and very especially preferably to 20 to 60 ppm by adding a calcium salt. However, the presence of calcium ions is not mandatory, and a series of liquefying enzymes for the liquefaction and saccharification are known which also yield good conversion rates and yields in the absence of calcium, so that, in such cases, the addition of calcium salts can be dispensed with.

To ensure an optimal activity of the starch-liquefying enzyme, the liquefaction is preferably carried out at the pH optimum of the liquefying enzyme, at least over some time, frequently at a pH in the weakly acidic range, as a rule in the range of from 4.0 to 7.0, preferably in the range of from 5.0 to 6.5, especially preferably in the range of from 5.3 to 6.0. The pH is usually adjusted before or at the beginning of the liquefaction process; this pH is, as a rule, checked during the liquefaction process and, if appropriate, readjusted. The pH is preferably adjusted with dilute mineral acids such as HCl, $HNO_3$, $H_2SO_4$ or $H_3PO_4$, with organic acids such as acetic acid, with alkali metal hydroxides such as NaOH or KOH, or with alkaline earth metal hydroxides such as magnesium hydroxide or calcium hydroxide. Preferably, the pH is adjusted with calcium hydroxide and/or sulfuric acid.

The maize flour suspension may be prepared batchwise or continuously, and any substances for adjusting the pH, such as calcium hydroxide and/or sulfuric acid, and the liquefying enzyme may be admixed to the water beforehand or may be added individually to the maize flour/water mixture. The substances may be added in any order. When the maize flour suspension is prepared batchwise, any type of stirred reactor may be employed. In the case of continuous production, slowly or fast operating continuous mixers will, as a rule, be employed.

The suspension (slurry) thus prepared will then be heated, preferably at a temperature above the gelling temperature of the starch employed. As a rule, a temperature in the range of from 80 to 120° C., preferably from 90 to 115° C. and especially preferably in the range of from 95 to 110° C. will be chosen, the temperature preferably being at least 5 K, in particular 10 K and especially preferably at least 20 K, for example 10 to 80 K, in particular 20 to 60 K, above the gelling temperature (gelatinization temperature). The liquefaction may also be carried out below the gelatinization temperature, for example using the enzymes or enzyme combinations described in WO 2004/113551.

In a preferred embodiment for liquefying the starch component, the slurry is first heated to a temperature above the gelatinization temperature of the starch by introducing direct steam. The mixture will typically be heated at a temperature which is at least 10 K and in particular at least 20 K, for example 10 to 80 K, in particular 20 to 60 K, above the gelatinization temperature in question. The suspension is preferably heated at temperatures in the range of from 80 to 120° C., in particular in the range of from 90 to 115° C. and especially in the range of from 95 to 110° C.

The direct steam employed for the heating process is typically superheated steam which has a temperature of at least 105° C., in particular at least 110° C., for example in the range from 110 to 210° C. However, the use of saturated steam is also possible. It is preferred to introduce the steam into the suspension at elevated pressure. Accordingly, the steam preferably has a pressure of at least 1.5 bar, for example 1.5 to 16 bar, in particular 2 to 12 bar.

As a rule, the introduction of direct steam into the suspension is carried out in such a way that the steam is introduced into the suspension at elevated pressure, preferably an elevated pressure of from 1 to 10 or 11 bar, in particular from 1.5 to 5 bar and preferably at high speed. As the result of the introduction of the steam, the suspension is instantly heated to temperatures above 90° C., that is to say to temperatures above the gelatinization temperature.

Heating with direct steam is preferably carried out in a continuously operating device into which the slurry is introduced continuously at a specific delivery pressure which is the result of the suspension's viscosity, the delivery speed and the geometry of the device, and into which device, in the delivery zone of the suspension, the hot steam is introduced at an elevated pressure relative to the delivery pressure, via a regulatable nozzle. Because the steam is introduced at elevated pressure, the suspension is not only heated, but mechanical energy is also introduced into the system, which promotes the further mixing of the maize flour particles, causes a particularly uniform supply of energy and, as a consequence, causes a particularly uniform gelatinization of the granular starch particles in the maize flour. These devices are typically tubular in geometry. The steam is preferably introduced along the longitudinal axis of the tubular device. As a rule, the suspension is fed at a flat angle relative to the steam jet, which angle will, as a rule, not exceed 50°. The regulatable nozzle typically has a conical geometry and tapers in the direction of the steam's flow. A pin, or a cone which is arranged on a longitudinally displaceable rod, is arranged inside this nozzle. The pin, or the cone, together with the cone of the nozzle, form a slot. By displacing the pin, or the rod, longitudinally, the size of the slot, and thus the cross-sectional area of the nozzle aperture can be adjusted in a simple manner, whereby the steam introduction rate can be regulated in a simple manner.

These devices are typically also equipped with a mixing tube into which the suspension is transported after the steam has been introduced, and in which the suspension is discharged from the device. This mixing tube is typically arranged in the direction in which the steam is introduced. Typically, the mixing tube together with the nozzle forms a slot through which the suspension is conveyed. As the result of this slot, additional shear forces act on the conveyed suspension which increase the supply of mechanical energy to the suspension. The mixing tube may be longitudinally displaceable. By displacing the mixing tube, the size of the slot aperture, and hence the pressure difference in the device, may be adjusted in a simple manner.

Such devices are known from the prior art as jet cookers, for example the device shown in "The Alcohol Textbook", chapter 2, loc. cit., FIG. 13, and commercially available, for example, under the name HYDROHEATER® or JetCooker® from Hydro Thermal Corp. Waukesha Wis., USA.

As a rule, the slurry which has been heated with direct steam is subsequently passed into an afterreaction zone in order to continue the gelling of the starch constituents. At the same time, the liquefying enzyme starts to hydrolyze the starch. Typically, an elevated pressure prevails in the afterreaction zone, typically an absolute pressure in the range of from 2 to 8 bar. The temperatures in the afterreaction zone are typically in the range of from 80 to 120° C., in particular in the range of from 90 to 115° C. The residence time in this afterreaction zone may be in the range of from 1 to 30 min, frequently 2 to 20 min, and in particular 5 to 10 min, depending on the temperature of the suspension. The afterreaction zones typically have a tubular or column geometry. In one embodiment, the afterreaction zone has the geometry of a horizontally arranged column. Here, the suspension which has left the steam treatment device is applied in the upper zone of the column and withdrawn in the bottom zone. In another embodiment of the invention, the afterreaction zone has a tubular geometry.

After the suspension has left the afterreaction zone, it is, as a rule, cooled, and a second liquefaction step is then carried out. Cooling may be performed by releasing the pressure of the solution, which is under pressure. Releasing the pressure is preferably carried out as a flash evaporation in order to cool the suspension, preferably down to temperatures of below 110° C., in particular below 105° C., for example in the range of from 80 to 110° C., preferably 90 to 105° C. and very especially preferably 95 to 100° C. As a rule, this is followed by a liquefaction of the starch thus digested, in a separate reaction vessel. If appropriate, it may be advantageous not to add all of the liquefying enzyme before or during the heating process, but to add a portion thereof to the second liquefaction step, after the temperature has been adjusted. This portion may amount to 0 to 80%, preferably 10 to 60% and very especially preferably 15 to 40% of the total amount of liquefying enzyme. The second liquefaction step may be carried out over a period of from 30 to 240 min, preferably 45 to 180 min and very especially preferably 60 to 120 min. The second liquefaction step may be effected in a continuous flow reactor, continuously in a cascade of stirred tank reactors, or in batchwise operating stirred tank reactors. When using tank reactors, it is advantageous to provide a sufficient number of tank reactors which permits individual tank reactors to be cleaned in parallel to the ongoing operation without losing capacity.

To fully degrade the starch to dextrins, the reaction mixture is held at the set temperature, or, if appropriate, heated further, until the detection of starch with iodine or, if appropriate, another test for detecting starch is negative or at least essentially negative. If appropriate, one or more further portions of α-amylase, for example in the range of from 0.001 to 0.5% by weight and preferably 0.002 to 0.2% by weight, based on the total amount of the starch source employed, may be added to the reaction mixture.

Instead of heating the slurry by means of direct steam, the former may also be heated at the desired temperature indirectly, using a heating medium, for example steam, in what are known as "Wide Gap" heat exchangers, which avoids the dilution of the maize flour suspension by the steam which has been introduced. Again, as a rule, an afterreaction and a second liquefaction will be carried out, as has been described for heating with direct steam. As regards the measures taken in this process, what has been said above also applies analogously here.

In this manner, an aqueous starch partial hydrolyzate is obtained which comprises the liquefied starch component from the maize flour, typically dextrins and, if appropriate, further oligosaccharides and mono- or disaccharides, and the protein components and, if appropriate, bran components, of the maize flour.

When the starch liquefaction is complete, a saccharification takes place of the dextrins present in the aqueous starch partial hydrolyzate, i.e. their degradation to give glucose and sucrose, respectively. The saccharification can be carried out continuously or batchwise, in a manner known per se.

The saccharification of the dextrins (i.e. oligosaccharides) in the liquefied starch solution is, as a rule, carried out enzymatically, i.e. with the aid of at least one enzyme which saccharifies the dextrins. In principle, all glucoamylases (enzyme class EC 3.2.1.3) may be employed for this purpose, in particular glucoamylases which have been obtained from *Aspergillus*, and specifically those which are used for the saccharification of substances obtained by dry milling processes in the context of bioethanol production. The glucoamylases which are suitable for the saccharification are also commercially available, for example from Novozymes under the name Dextrozyme GA; or from Genencor under the name Optidex. A combination of different glucoamylases may also be used.

The at least one saccharifying enzyme, in particular at least one glucoamylase, is added to the dextrin-containing liquid medium obtained after the liquefaction in an amount of usually 0.001 to 5.0% by weight, preferably 0.005 to 3.0% by weight and especially preferably 0.01 to 1.0% by weight, based on the total amount of the starch source employed.

As a rule, the liquefied starch solution is cooled, or brought, usually to the temperature optimum of the saccharifying enzyme or slightly below, for example to 40 to 70° C., preferably 50 to 65° C. and in particular 60 to 63° C., and subsequently treated with the saccharifying enzyme. The aqueous starch partial hydrolyzate is preferably subjected to a saccharification process immediately after the liquefaction process. The hot aqueous starch partial hydrolyzate is then cooled to the abovementioned temperatures, and only then is the saccharifying enzyme added. This cooling is advantageously carried out in a heat exchanger, where the energy released may be exploited for prewarming other process streams.

The saccharification is advantageously carried out at a pH in the optimum activity range of the enzyme employed, preferably at a pH in the range of from 3.0 to 5.5, in particular in the range of from 4.0 to 5.0 and especially preferably in the range of from 4.2 to 4.8. The pH is preferably brought to the desired value before the saccharifying enzyme, in particular the glucoamylase, is added.

The saccharification can be effected batchwise in stirred tank reactors or continuously in a flow tube or especially preferably in a cascade of stirred tank reactors. When using tank reactors, it is advantageous to provide a sufficient number of tank reactors which permits individual tank reactors to be cleaned in parallel to the ongoing operation without losing capacity.

After the addition of the saccharifying enzyme, the dextrin-containing suspension is held at the temperature adjusted, preferably over a period of, for example, 8 to 72 h or longer, if required, frequently 12 to 60 h, preferably 24 to 54 h and especially preferably 36 to 48 h, during which process the dextrins are saccharified to give mono- and disaccharides. The progress of the saccharification reaction can be monitored using methods known to the skilled worker, for example HPLC, enzyme assays or glucose test sticks. The saccharification has ended when the concentration of the monosaccharides no longer increases noticeably, or when it drops again.
Step c):

The saccharification gives an aqueous glucose solution which, besides glucose, additionally comprises the nonhydrolyzed constituents of the maize flour as solids in suspended form. These solids are mainly a high-protein solid, which is here and hereinbelow referred to as maize gluten, and, if the bran has been recirculated during the milling stage, bran constituents. These constituents are depleted from the glucose solution in step c) of the process according to the invention. Here, a procedure may be followed in which all of the glucose solution produced in step b) and comprising maize gluten is subjected to a solids separation process. However, it is also possible only to subject a partial stream of the glucose solution prepared in step b) and comprising maize gluten to a solids separation process and to utilize the remaining glucose which comprises maize gluten for another purpose, for example the production of bioethanol.

As a rule, a depletion is carried out to the extent that at least 80% by weight, preferably at least 90% by weight and in particular at least 95% by weight of the gluten constituents or bran constituents which are present in the glucose solution are removed.

Removal of the maize gluten and of the bran which may be present may be effected via any known solid/liquid separation process, with mechanical processes such as centrifugation, decanting and filtration, including combinations of these measures, being preferred.

To remove the solids from the glucose solution, it has proved advantageous when the glucose solution subjected to the removal stage has a temperature in the range of from 60 to 100° C., in particular in the range of from 70 to 90° C. and especially preferably in the range of from 75 to 85° C. To this end, the glucose solution obtained in step b) will, as a rule, be warmed to the desired temperature before the solid constituents gluten and bran are depleted. The warming process is advantageously carried out in a heat exchanger, where the energy required may be used for cooling other process streams.

It has furthermore proved advantageous when the pH of the glucose solution is brought to a value in the range of from 4.0 to 6.5, in particular in the range of from 4.5 to 6.0 and especially preferably in the range of from 5.0 to 5.5, before the solids are depleted. Any base, but preferably an alkali metal hydroxide, for example aqueous sodium hydroxide solution, or ammonia, may be employed for adjusting the pH.

The depletion process gives a low-solid glucose solution and a high-solid fraction which comprises the maize gluten and, if appropriate, bran constituents and which has a lower glucose content than the glucose solution which is low in solids.

The low-solid glucose solution may still comprise small amounts of undissolved solid, which amount, as a rule, does not exceed 15% by volume, in particular 10% by volume and specifically 5% by volume, based on the total volume of the aqueous glucose solution, and which is frequently in the range of from 0.001 to 15% by volume, in particular in the range of from 0.01 to 10% by volume and especially preferably in the range of from 0.02 to 5% by volume, based on the total volume of the aqueous glucose solution. The undissolved solid is determined by centrifuging the glucose solution in graduated centrifuge tubes at 1650 g for 15 min and subsequently reading the amount of undissolved solid.

To obtain a high glucose yield, it is advantageous when the high-solid fraction obtained as a result of the solid/liquid separation is resuspended in water and then subjected to another solid/liquid separation. The amount of water is typically in the range of from 3 to 15 l/kg suspended solid, calculated as dry matter, or in the range of from 3 to 20 l per 1 moist, separated solid. This second solid/liquid separation gives a liquid phase which comprises some of the glucose obtained in the solid phase of the first solid/liquid separation in dissolved form. The liquid phase is then combined with the liquid phase of the first solid/liquid separation. To further increase the glucose yield, this procedure, i.e. the resuspending of the resulting solid in water and the subsequent solid/liquid separation, may be repeated once or more than once, where the resulting aqueous glucose solutions are in each case combined with the glucose solution obtained in the first solid/liquid separation.

The temperature at which the second and the, if appropriate, further solid/liquid separation(s) are carried out is typically in the range of from 60 to 100° C., preferably in the range of from 70 to 90° C. and especially preferably in the range of from 75 to 85° C. As regards the pH, what has been said above for the first solid/liquid separation also applies here.

The water which is used for resuspending the high-solid fraction of the first and the further solid/liquid separations may be fresh water. Frequently, however, the aqueous glucose solution of a later solid/liquid separation will be employed for the resuspending step in order firstly to reduce the dilution, by fresh water, of the combined low-solid glucose solutions of the individual solid/liquid separation steps and secondly to reduce the overall requirements of fresh water. In three successive solid/liquid separations, for example, the liquid phase of the third solid/liquid separation will be used for resuspending the solid phase of the second solid/liquid separation, and the liquid phase of the second solid/liquid separation will be used for resuspending the high-solid phase of the first solid/liquid separation. However, it is also possible to employ, besides the fresh water, process water which is generated for example later, as a condensate when the glucose solution is evaporated, or which is generated when the secondary products (for example maize gluten or biomass) are dried.

To further reduce the solids in the resulting aqueous glucose solutions, it may be advantageous to subject the latter to what is known as a polishing step, in order to deplete further solids which are present therein. The further depletion may be carried out via any known solid/liquid separation route, such as, for example, membrane filtration, including microfiltration and ultrafiltration, conventional filtration, floatation, centrifugation, decanting or separating. Multi-step use forms which are the result of any desired combination of the methods mentioned here, are also feasible.

The low-solid glucose solution which can be obtained from the aqueous glucose obtained in step b) after depletion of the maize gluten and, if appropriate, bran present is novel and particularly suitable for the production of chemicals. Accordingly, the aqueous glucose solution is also subject matter of the present application.

The dry-matter content is understood as meaning the total amount of dissolved and undissolved solids in the aqueous glucose solution. These solids can be determined in the known manner by evaporating the glucose solution. To this end, a certain amount of the glucose solution in question is evaporated to dryness at 80° C. in the drying oven. Weighing the dry residue gives the dry-matter content. As an alternative, it is possible to employ drying scales as are commercially available for this purpose for example from PCE Deutschland, Meschede.

Based on the solids present in the aqueous glucose solution, the aqueous glucose solution has the following characteristic constituents:
a) 80 to 98% by weight, preferably 93 to 97% by weight, of sugars in the form of glucose and, optionally, disaccharides such as sucrose, maltose and isomaltose,
b) 1 to 7% by weight, frequently 2 to 7% by weight, preferably 2.5 to 5% by weight, of crude protein,
c) 0.001 to 0.1% by weight, frequently 0.01 to 0.1% by weight of crude fiber,
d) 200 to 1500 mg/kg, preferably 600 to 1200 mg/kg, of free amino acids, and
e) 0.01 to 1% by weight of crude ash constituents.

A glucose solution with such a composition is novel and also subject matter of the present invention.

Besides, the glucose solution may still comprise small amounts of oil/fat from the germ fraction. The majority of any oil/fat constituents, however, will as a rule be separated in step c), together with the gluten. The same applies to any bran constituents which have not been separated before the saccharification process.

The invention furthermore relates to the maize gluten generated in step c) of the process according to the invention. It is generated in the process according to the invention in an amount of from 4 to 40% by weight, in particular 8 to 30% by weight, based on the dry matter of the maize employed. As a rule, the maize gluten has the following gross composition, the data relating in each case to the total dry matter of the maize gluten.
a) 10 to 60% by weight, in particular 20 to 55% by weight, of crude protein;
b) 1 to 60% by weight, in particular 2 to 45% by weight, of sugar constituents;
c) up to 20% by weight, frequently 0.5 to 10% by weight, of crude fat, vegetable fats and/or vegetable oils;
d) up to 20% by weight, in particular 1 to 12% by weight, of crude fiber constituents; and
e) up to 15% by weight, for example 0.1 to 10% by weight, of other solid constituents, also referred to as crude ash.

The maize gluten which has been separated off in step c) is a finely particulate solid which, as a rule, has a moisture content in the range of from 50 to 85% by weight after its separation, in particular in the range of from 55 to 75% by weight, based on the total weight of the maize gluten which has been separated. The maize gluten can be dried in the known manner to give a finely particulate nontacky powder which produces no or little dust. The moisture content here is typically below 50% by weight, as a rule below 30% by weight and specifically below 15% by weight. A moist maize gluten with a dry-matter content of 35% by weight, or a water content of 185%, based on the dry maize gluten, behaves like a solid.

The mean particle size of the maize gluten particles (weight average, determined by light diffraction or screen analysis) is typically in the range of from 50 to 600 µm and in particular in the range of from 100 to 500 µm.

The maize gluten according to the invention has a high water absorption capacity and is capable of absorbing up to 185% by weight of water based on its dry weight, without becoming tacky in the process. It is therefore particularly suitable as a formulation auxiliary, in particular for the preparation of solid formulations of moist or pasty substances which, in turn, tend to agglutination. In particular, the maize gluten according to the invention is suitable for the formulation of a biomass as generated in a fermentation. In this manner, a nontacky product comprising biomass and maize gluten is obtained, and this product may be employed for example as a feedstuff or a component feedstuffs.

Moreover, the maize gluten according to the invention is distinguished by a high absorption capacity for oils and oil-like substances, in particular for vegetable oils. It is therefore particularly suitable for the preparation of solid formulations of superior vegetable oils or vegetable oil constituents or substances with comparable properties, such as tocopherols.

The aqueous glucose obtained after the solid/liquid separation(s) may, if appropriate, be concentrated to the desired glucose concentration in a one- or multi-step evaporation process. To this end, the aqueous glucose solution will be concentrated at temperatures in the range of from 50 to 100° C., preferably in the range of from 70 to 95° C. and especially preferably in the range of from 80 to 90° C., preferably with the application of a vacuum. The concentrating will preferably be performed until a glucose concentration of at least 40% by weight, in particular at least 50% by weight and especially preferably at least 55% by weight is obtained, for example in the range of from 40 to 80% by weight, preferably in the range of from 50 to 70% by weight and very especially preferably in the range of from 55 to 65% by weight.

Use of the Glucose for the Production of Organic Substances

The glucose solution thus obtained can subsequently be used as a carbon source for the production of organic substances, i.e. chemicals.

The term chemicals is to be interpreted broadly and comprises all organic substances, i.e. defined compounds, but also oligomers, polymers, including enzymes, but also biomass such as, for example, yeasts or single cell protein, which are produced, or can be produced, with glucose as the starting material. The organic substance may be produced both via fermentation and via the nonfermentative route. The process according to the invention has advantages in particular in the production of chemicals other than ethanol since, as a rule, the glucose quality must meet higher requirements in this case.

Examples of organic substances which can be produced from glucose via the nonfermentative route comprise 5-hydroxymethylfurfural, laevulic acid, gluconic acid, glucuronic acid, 2-ketogluconic acid, glutaric acid, sorbitol, isosorbide and alkylpolyglucosides, polyols such as ethylene glycol, propylene glycol and HFCS (High-Fructose Corn Syrup).

Examples of organic substances which can be produced from glucose via the fermentative route:
mono-, di- and tricarboxylic acids which have 2 to 10 carbon atoms and which optionally have hydroxyl groups attached to them, for example tartaric acid, itaconic acid, succinic acid, acetic acid, propionic acid, lactic acid, 3-hydroxypropionic acid, fumaric acid, maleic acid, 2,5-furandicarboxylic acid, glutaric acid, laevulic acid, gluconic acid, aconitic acid, diaminopimelic acid and citric acid;

proteinogenic and nonproteinogenic amino acids, for example lysine, glutamate, methionine, phenylalanine, aspartic acid, tryptophan and threonine;

purine bases and pyrimidine bases;

nucleosides and nucleotides, for example nicotinamide adenine dinucleotide (NAD) and adenosine-5'-monophosphate (AMP);

lipids, saturated and unsaturated fatty acids having preferably 10 to 22 carbon atoms, for example γ-linolenic acid, dihomo-γ-linolenic acid, arachidonic acid, eicosapentaenoic acid and docosahexaenoic acid;

diols having 3 to 10 carbon atoms, for example propanediol and butanediol;

polyhydric alcohols having 3 or more hydroxyl groups, for example 3, 4, 5 or 6 OH groups, for example glycerol, sorbitol, mannitol, xylitol and arabinitol;

long-chain alcohols having at least 4 carbon atoms, for example 4 to 22 carbon atoms, for example butanol; carbohydrates, for example hyaluronic acid and trehalose;

carbohydrates;

aliphatic amines, in particular aliphatic diamines having 3 to 10 carbon atoms, such as 1,5-pentanediamine;

aromatic compounds, for example aromatic amines, vanillin and indigo;

vitamins and provitamins, for example ascorbic acid, vitamin $B_6$, vitamin $B_{12}$ and riboflavin;

cofactors and nutraceuticals;

proteins, for example enzymes, such as amylases, pectinases, acid, hybrid or neutral cellulases, esterases such as lipases, pancreases, proteases, xylanases and oxidoreductases such as laccase, catalase and peroxidase, glucanases and phytases;

yeasts, for example baker's yeasts or brewer's yeasts;

carotenoids, for example lycopene, β-carotene, astaxanthin, zeaxanthin and canthaxanthin;

ketones having 3 to 10 carbon atoms, for example acetone and acetoin;

lactones, for example γ-butyrolactone;

polyhydroxyalkanoates, for example polyhydroxyacetate;

polylactides;

polysaccharides, for example glucan, mannan, galactan;

polyisoprenoids;

polyamides and cyclodextrins.

The term "cofactor" comprises nonproteinaceous compounds which are required for the occurrence of a normal enzyme activity. These compounds can be organic or inorganic; preferably, the cofactor molecules of the invention are organic. Examples of such molecules are NAD and nicotinamide adenine dinucleotide phosphate (NADP); the precursor of these cofactors is niacin.

The term "nutraceutical" comprises food additives which are constitutional in plants and animals, in particular humans. Examples of such molecules are vitamins, antioxidants and certain lipids, for example polyunsaturated fatty acids.

Use of the Glucose in a Fermentation

A preferred subject matter of the invention is the use of the glucose solution obtainable in accordance with the invention as a glucose source for the fermentative production of an organic substance as defined above.

Accordingly, a further subject matter of the invention is a process for the production of an organic substance by fermentation, comprising the following steps:

i. Providing an aqueous glucose solution according to the invention, for example by producing the glucose solution in accordance with the process according to the invention, and ii. Adding the glucose solution to a fermentation medium which comprises a microorganism which enables overproducing the organic substance.

The fermentation can be carried out in the usual manner with which the skilled worker is familiar. To this end, the desired microorganism in each case will, as a rule, be cultured using an aqueous glucose produced in accordance with the invention.

The fermentation process can be operated both batchwise (in the batch mode) and in the fed-batch mode (including fed batch with intermediate harvesting), the fed-batch mode being preferred.

For example, the aqueous glucose solution obtained in accordance with the process according to the invention—if appropriate together with a conventional sugar source, i.e. metabolizable mono-, di- and/or oligosaccharides or the composition which comprises metabolizable mono-, di- and/or oligosaccharides in a concentration of at least 45% by weight and which is typically essentially free from solids which are insoluble in water, for example low-quality molasses with 45 and 50% by weight of sugar—if appropriate after dilution with water and addition of customary media components such as buffers, nutrient salts, nitrogen sources such as ammonium sulfate, urea and the like, complex nutrient media components comprising amino acids, such as yeast extracts, peptones, CSL and the like, may be inoculated with the desired microorganism and the latter may be multiplied under fermentation conditions until the microorganism concentration reaches the stationary state which is desired for the fermentation. Here, the sugars present in the glucose solution according to the invention are metabolized and the desired product of interest is formed (also known as batch mode of operation or batch phase).

Owing to the large amount of free amino acids in the glucose according to the invention, the addition of further complex nutrient media components can, surprisingly, be dispensed with, or their amount can be reduced drastically, which is a further advantage of the glucose solution according to the invention.

In the fed-batch mode of operation, the fermentation process will be continued by adding the glucose which is obtainable in accordance with the invention. In doing so, the metabolite overproduced by the microorganism is accumulated in the fermentation liquor, it being possible for the metabolite to be present both in the cells of the microorganism and in the aqueous phase of the fermentation medium.

The fermentation will preferably be carried out in the fed-batch mode of operation. Here, a procedure will be followed in which the microorganism is first multiplied using a glucose solution according to the invention and/or another sugar source until the desired microorganism concentration in the fermenter has been reached. Thereafter, the aqueous glucose according to the invention is used to charge the fermenter. This maintains the fermentation process, and the metabolite which is overproduced by the microorganism accumulates in the fermentation liquor (see above). The sugar content in the fermentation liquor may be regulated in particular via the feed rate of the aqueous glucose according to the invention. As a rule, the feed rate will be adjusted such that the glucose concentration in the fermentation liquor is in the range of from >0% by weight to approximately 5% by weight and in particular does not exceed a value of 3% by weight.

If appropriate, the glucose according to the invention can be sterilized before the fermentation, during which process the contaminating microorganisms are destroyed, usually by thermal processes. To this end, the sugar-containing liquid medium is heated, conventionally to temperatures above 80° C. The destruction or lysis of the contaminants may be effected immediately before the fermentation. To this end, all of the sugar-containing liquid medium is subjected to sterilization.

In particular, the invention relates to a process for the production of organic nonvolatile compounds having at least 3 carbon atoms or having at least 2 carbon atoms and at least 1 nitrogen atom. In this context, nonvolatile organic compounds are understood as meaning those compounds which cannot be obtained from the fermentation liquor via distillation without undergoing decomposition. As a rule, these compounds have a boiling point above the boiling point of water, frequently above 150° C. and in particular above 200° C. under atmospheric pressure. As a rule, these are compounds which are in the solid state under standard conditions (298 K, 101.3 kPa).

However, it is also possible to employ the sugar-containing liquid medium according to the invention in a fermentation for the production of nonvolatile metabolites which, under atmospheric pressure, have a melting point below the boiling point of water or/and an oily consistency.

The process according to the invention is particularly suitable for the production of enzymes, amino acids, vitamins, nucleotides, di-, oligo- and polysaccharides, aliphatic mono- and dicarboxylic acids having 3 to 10 carbon atoms, aliphatic hydroxycarboxylic acids having 3 to 10 carbon atoms, ketones having 3 to 10 carbon atoms, alkanols having 4 to 10 carbon atoms and alkanediols having 3 to 10 and in particular 3 to 8 carbon atoms, and amines, in particular aliphatic diamines having 3 to 10 carbon atoms.

It is clear to the skilled worker that the compounds produced thus by way of fermentation are obtained in each case in the enantiomeric form produced by the microorganisms employed (if different enantiomers exist). Thus, for example, the amino acids are, as a rule, obtained in the form of the respective L enantiomers.

The microorganisms employed in the fermentation depend in a manner known per se on the metabolites in question, as specified in detail hereinbelow. They can be of natural origin or genetically modified. Examples of suitable microorganisms and fermentation processes are those given in Table A hereinbelow.

TABLE A

| Substance | Microorganism | Reference |
|---|---|---|
| Tartaric acid | Lactobacilli, (for example Lactobacillus delbrueckii) | Rehm, H.-J.: Biotechnology, Weinheim, VCH, 1980 and 1993-1995; Gutcho, Chemicals by Fermentation, Noyes Data Corporation (1973), |
| Itaconic acid | Aspergillus terreus, Aspergillus itaconicus | Jakubowska, in Smith and Pateman (Eds.), Genetics and Physiology of Aspergillus, London: Academic Press 1977; Miall, in Rose (Ed.), Economic Microbiology, Vol. 2, pp. 47-119, London: Academic Press 1978; U.S. Pat. No. 3,044,941 (1962). |
| Succinic acid | Actinobacillus sp. 130Z, Anaerobiospirillum succiniproducens, Actinobacillus succinogenes, E. coli | Int. J. Syst. Bacteriol. 26, 498-504 (1976); EP 249773 (1987), Inventors: Lemme and Datta; U.S. Pat. No. 5,504,004 (1996), Inventors: Guettler, Jain and Soni; Arch. Microbiol. 167, 332-342 (1997); Guettler MV, Rumler D, Jain MK., Actinobacillus succinogenes sp. nov., a novel succinic-acid-producing strain from the bovine rumen. Int J Syst Bacteriol. 1999 Jan; 49 Pt 1: 207-16; U.S. Pat. No. 5,723,322, U.S. Pat. No. 5,573,931, U.S. Pat. No. 5,521,075, WO99/06532, U.S. Pat. No. 5,869,301, U.S. Pat. No. 5,770,435 |
| Hydroxypropionic acid | Lactobacillus delbruckii, L. leichmannii or Sporolactobacillus inulinus | RÖMPP Online Version 2.2 |
| Propionic acid | Propionibacterium, for example P. arabinosum, P. schermanii, P. freudenreichii, Clostridium propionicum, | Rehm, H.-J.: Biotechnology, Weinheim, VCH, 1980 and 1993-1995; Gutcho, Chemicals by Fermentation, Noyes Data Corporation (1973), |
| Diaminopimelic acid | Corynebacterium glutamicum | Rehm, H.-J.: Biotechnology, Weinheim, VCH, 1980 and 1993-1995; Gutcho, Chemicals by Fermentation, Noyes Data Corporation (1973), |
| Citric acid | Aspergillus niger, Aspergillus wentii | Crit. Rev. Biotechnol. 3, 331-373 (1986); Food Biotechnol. 7, 221-234 (1993); 10, 13-27 (1996). |
| Aconitic acid | Aspergillus niger, Aspergillus wentii | Crit. Rev. Biotechnol. 3, 331-373 (1986); Food Biotechnol. 7, 221-234 (1993); 10, 13-27 (1996).; Rehm, H.-J.: Biotechnology, Weinheim, VCH, 1980 and 1993-1995; |
| Malic acid | Aspergilli, for example Aspergillus flavus, A. niger, A. oryzae, Corynebacterium | U.S. Pat. No. 3,063,910 |
| Gluconic acid | Aspergilli, for example A. niger | Gutcho, Chemicals by Fermentation, Noyes Data Corporation (1973), |

TABLE A-continued

| Substance | Microorganism | Reference |
|---|---|---|
| Butyric acid | *Clostridium* (for example *Clostridium acetobutylicum*, *C. butyricum*) | Rehm, H.-J.: Biotechnology, Weinheim, VCH, 1980 and 1993-1995; |
| Lactic acid | *Lactobacillus* for example *L. delbruckii*, *L. leichmannii*, | Rehm, H.-J.: Biotechnology, Weinheim, VCH, 1980 and 1993-1995; |
| Lysine | *Corynebacterium glutamicum* | Ikeda, M.: Amino Acid Production Process (2003), Adv. Biochem. Engin/Biotechnol 79, 1-35. |
| Glutamate | *Corynebacterium glutamicum* | Ikeda, M.: Amino Acid Production Process (2003), Adv. Biochem. Engin/Biotechnol 79, 1-35. |
| Methionine | *Corynebacterium glutamicum* | Ikeda, M.: Amino Acid Production Process (2003), Adv. Biochem. Engin/Biotechnol 79, 1-35. |
| Phenylalanine | *Corynebacterium glutamicum*, *E. coli* | Trends Biotechnol. 3, 64-68 (1985); J. Ferment. Bioeng. 70, 253-260 (1990). |
| Threonine | *E. coli* | Ikeda, M.: Amino Acid Production Process (2003), Adv. Biochem. Engin/Biotechnol 79, 1-35. |
| Aspartic acid | *E. coli* | Ikeda, M.: Amino Acid Production Process (2003), Adv. Biochem. Engin/Biotechnol 79, 1-35 and references cited therein, Gutcho, Chemicals by Fermentation, Noyes Data Corporation (1973) |
| Purine and pyrimidine bases | *Bacillus subtilis* | Rehm, H.-J.: Biotechnology, Weinheim, VCH, 1980 and 1993-1995; Gutcho, Chemicals by Fermentation, Noyes Data Corporation (1973), |
| Nicotinamide adenine dinucleotide (NAD) | *Bacillus subtilis* | Rehm, H.-J.: Biotechnology, Weinheim, VCH, 1980 and 1993-1995; Gutcho, Chemicals by Fermentation, Noyes Data Corporation (1973), |
| Adenosine-5'-monophosphate (AMP) | *Bacillus subtilis* | Rehm, H.-J.: Biotechnology, Weinheim, VCH, 1980 and 1993-1995; Gutcho, Chemicals by Fermentation, Noyes Data Corporation (1973), |
| γ-Linolenic acid | *Mucor*, *Mortiella*, *Aspergillus* spp. | Gill, I., Rao, V.: Polyunsaturated fatty acids, part 1: occurrence, biological activities and applications (1997). Trends in Biotechnology 15 (10), 401-409; Zhu, H.: Utilization of Rice Bran by *Pythium* irregulare for Lipid Production. Master Thesis Louisiana State University, Oct. 31, 2002 (URN etd-1111102-205855). |
| Dihomo-γ-linolenic acid | *Mortiella*, *Conidiobolus*, *Saprolegnia* spp. | Gill, I., Rao, V.: Polyunsaturated fatty acids, part 1: occurrence, biological activities and applications (1997). Trends in Biotechnology 15 (10), 401-409; Zhu, H.: Utilization of Rice Bran by *Pythium* irregulare for Lipid Production. Master Thesis Louisiana State University, Oct. 31, 2002 (URN etd-1111102-205855). |
| Arachidonic acid | *Mortiella*, *Phytium* spp. | Gill, I., Rao, V.: Polyunsaturated fatty acids, part 1: occurrence, biological activities and applications (1997). Trends in Biotechnology 15 (10), 401-409; Zhu, H.: Utilization of Rice Bran by *Pythium* irregulare for Lipid Production. Master Thesis Louisiana State University, Oct. 31, 2002 (URN etd-1111102-205855). |
| Eicosapentaenoic acid | *Mortiella*, *Phytium* spp., *Rhodopseudomonas*, *Shewanella* spp. | Gill, I., Rao, V.: Polyunsaturated fatty acids, part 1: occurrence, biological activities and applications (1997). Trends in Biotechnology 15 (10), 401-409; Zhu, H.: Utilization of Rice Bran by *Pythium* irregulare for Lipid Production. Master Thesis Louisiana State University, Oct. 31, 2002 (URN etd-1111102-205855). |
| Docosahexaenoic acid | *Thraustochytrium*, *Entomophthora* spp., *Rhodopseudomonas*, *Shewanella* spp. | Gill, I., Rao, V.: Polyunsaturated fatty acids, part 1: occurrence, biological activities and applications (1997). Trends in Biotechnology 15 (10), 401-409; Zhu, H.: Utilization of Rice Bran by *Pythium* irregulare for Lipid Production. Master Thesis Louisiana State University, Oct. 31, 2002 (URN etd-1111102-205855). |
| Propanediol | *E. coli* | DE 3924423, US 440379, WO 9635799, U.S. Pat. No. 5,164,309 |
| Butanediol | *Enterobacter aerogenes*, *Bacillus subtilis*, *Klebsiella oxytoca* | Rehm, H.-J.: Biotechnology, Weinheim, VCH, 1980 and 1993-1995; Gutcho, Chemicals by Fermentation, Noyes Data Corporation (1973); H. G. SCHLEGEL and H. W. JANNASCH, 1981; Afschar et al.: Mikrobielle Produktion von 2,3-Butandiol, CIT 64 (6), 2004, 570-571 |
| Butanol | *Clostridium* (for example *Clostridium acetobutylicum*, *C. propionicum*) | Rehm, H.-J.: Biotechnology, Weinheim, VCH, 1980 and 1993-1995; Gutcho, Chemicals by Fermentation, Noyes Data Corporation (1973), |
| Glycerol | Yeast, *Saccharomyces rouxii* | Gutcho, Chemicals by Fermentation, Noyes Data Corporation (1973), |

TABLE A-continued

| Substance | Microorganism | Reference |
|---|---|---|
| Mannitol | *Aspergillus candida, Torulopsis mannitofaciens* | Gutcho, Chemicals by Fermentation, Noyes Data Corporation (1973), |
| Arabitol | *Saccharomyces rouxii, S. mellis, Sclerotium glucanicum, Pichia ohmeri* | Gutcho, Chemicals by Fermentation, Noyes Data Corporation (1973), |
| Xylitol | *Saccharomyces cerevisiae* | Gutcho, Chemicals by Fermentation, Noyes Data Corporation (1973), |
| Hyaluronic acid | *Streptococcus* sp. | Rehm, H.-J.: Biotechnology, Weinheim, VCH, 1980 and 1993-1995; |
| Trehalose | *Brevibacterium, Corynebacterium, Microbacterium, Arthrobacter* spp., *Pleurotus genus, Filobasidium floriforme* | JP 05099974, JP 06311891, FR 2671099, EP 0555540, JP 3053791, Miyazaki, J.-I., Miyagawa, K.-I., Sugiyama, Y.: *Trehalose Accumulation* by Basidiomycotinous Yeast, *Filobasidium floriforme*. Journal of Fermentation and Bioengineering 81, (1996) 4, 315-319. |
| Ascorbic acid | *Gluconobacter melanogenes* | RÖMPP Online Version 2.2 |
| Vitamin $B_{12}$ | *Propionibacterium* spp., *Pseudomonas denitrificans* | Chem. Ber. 1994, 923-927; RÖMPP Online Version 2.2 |
| Riboflavin | *Bacillus subtilis, Ashbya gossypii* | WO 01/011052, DE 19840709, WO 98/29539, EP 1186664; Fujioka, K.: New biotechnology for riboflavin (vitamin $B_2$) and character of this riboflavin. Fragrance Journal (2003), 31(3), 44-48. |
| Vitamin $B_6$ | *Rhizobium tropici, R. meliloti* | EP0765939 |
| Enzymes | *Aspergilli* (for example *Aspergillus niger, A. oryzae), Trichoderma, E. coli, Hansenlula* or *Pichia* (for example *Pichia pastorius), Bacillus* (for example *Bacillus licheniformis, B. subtilis*) and many others | Rehm, H.-J.: Biotechnology, Weinheim, VCH, 1980 and 1993-1995; Gutcho, Chemicals by Fermentation, Noyes Data Corporation (1973), |
| Zeaxanthin | *Dunaliella salina* | Jin et al (2003) Biotech. Bioeng. 81: 115-124 |
| Canthaxanthin | *Brevibacterium* | Nelis et al (1991) J Appl Bacteriol 70: 181-191 |
| Lycopene | *Blakeslea trispora, Candida utilis* | WO 03/056028, EP 01/201762, WO 01/12832, WO 00/77234, Miura et al (1998) Appl Environ Microbiol 64: 1226-1229 |
| β-Carotene | *Blakeslea trispora, Candida utilis* | Kim S., Seo W., Park Y., Enhanced production of beta-carotene from *Blakeslea trispora* with Span 20, Biotechnology Letters, Vol 19, No 6, 1997, 561-562; Mantouridou F., Roukas T.: Effect of the aeration rate and agitation speed on beta-carotene production and morphology of *Blakeslea trispora* in a stirred tank reactor: mathematical modelling, Biochemical Engineering Journal 10 (2002), 123-135; WO 93/20183; WO 98/03480, Miura et al (1998) Appl Environ Microbiol 64: 1226-1229 |
| Astaxanthin | *Phaffia rhodozyma; Candida utilis* | U.S. Pat. No. 5,599,711; WO 91/02060, Miura et al (1998) Appl Environ Microbiol 64: 1226-1229 |
| Polyhydroxy-alkanoates, polyesters | *Escherchia coli, Alcaligenes latus*, and many others | S. Y. Lee, Plastic Bacteria, Progress and Prospects for polyhydroxyalkanoate production in bacteria, Tibtech, Vol. 14, (1996), pp. 431-438., Steinbüchel, 2003: Steinbüchel (Ed.), Biopolymers, 1st ed., 2003 Wiley-VCH, Weinheim and references cited therein |
| Polysaccharides | *Leuconostoc mesenteroides, L. dextranicum, Xanthomonas campestris*, and many others | Rehm, H.-J.: Biotechnology, Weinheim, VCH, 1980 and 1993-1995; Gutcho, Chemicals by Fermentation, Noyes Data Corporation (1973), |
| Polyisoprenoids | *Lactarius* sp., *Hygrophorus* sp., *Russula* sp. | Steinbüchel (Ed.), Biopolymers, 1st ed., 2003, Wiley-VCH, Weinheim and references cited therein |
| Acetone | *Clostridium* (for example. *Clostridium acetobutylicum, C. propionicum*) | Rehm, H.-J.: Biotechnology, Weinheim, VCH, 1980 and 1993-1995; Gutcho, Chemicals by Fermentation, Noyes Data Corporation (1973) |
| Acetoin | *Enterobacter aerogenes, Clostridium* | Lengeler, J. W., Drews, G., Schlegel, H.G.: Eds., Biology of the Procaryotes, Thieme, Stuttgart (1999), p. 307; RÖMPP Online-Edition |

TABLE A-continued

| Substance | Microorganism | Reference |
|---|---|---|
| Vanillin | acetobutylicum, Lactococcus lactis Pseudomonas putida, Amycolatopsis sp. | Priefert, H., Rabenhorst, J., Steinbüchel, A. Biotechnological production of vanillin. Appl. Microbiol. Biotechnol. 56, 296-314 (2001) |
| Thurigensin | Bacillus thuringiensis | Jian-Zhong Jong et al.: Fed-batch culture of Bacillus thuringiensis for thuringensin production in a tower type bioreactor. Biotechnology and Bioengineering 48 (3) (2004), 207-213. |
| Polyketides | Streptomyces fradiae, Sorangium cellulosum | Kirst: Fermentation-derived compounds as a source for new products. Pure & Appl. Chem. 70 (2), (1998), 335-338; Zirkle et al.: Heterologous production of the antifungal polyketide antibiotic soraphen A of Sorangium cellulosum So ce26 in Streptomyces lividans. Microbiology 150 (8), (2004), 2761-74. |
| Gibberellic acid | Gibberella fujikuroi | Hollmann et al.: Extraktiv-Fermentation von Gibberellinsäure mit Gibberella fujikuroi. CIT 7 (1995), 892-895. |
| Indigo | Escherichia coli JB 102 | Berry, A., Dodge, T. C., Pepsin, M., Weyler, W.: Application of metabolic engineering to improve both the production and use of biotech indigo. Journal of Industrial Microbiology & Biotechnology 28 (2002), 127-133. |

In preferred embodiments of the invention, the organic compound produced is selected from among mono-, di- and tricarboxylic acids which have 3 to 10 carbon atoms and which optionally have hydroxyl groups attached to them, proteinogenic and nonproteinogenic amino acids, purine bases, pyrimidine bases; nucleosides, nucleotides, lipids; saturated and unsaturated fatty acids; diols having 4 to 10 carbon atoms, polyhydric alcohols having 3 or more hydroxyl groups, long-chain alcohols having at least 4 carbon atoms, carbohydrates, in particular di-, oligo- and polysaccharides, aromatic compounds, vitamins, provitamins, cofactors, nutraceuticals, proteins, carotenoids, ketones having 3 to 10 carbon atoms, lactones, amines, biopolymers and cyclodextrins.

A first preferred embodiment of the invention relates to the use of the sugar-containing liquid medium which is obtainable in accordance with the invention in a fermentative production of enzymes such as phytases, xylanases or glucanases.

A second preferred embodiment of the invention relates to the use of the sugar-containing liquid medium which is obtainable in accordance with the invention in a fermentative production of amino acids such as lysine, methionine, threonine or glutamate.

A further preferred embodiment of the invention relates to the use of the sugar-containing liquid medium which is obtainable in accordance with the invention in a fermentative production of vitamins such as pantothenic acid and riboflavin, and their precursors and derivatives.

Further preferred embodiments of the invention relate to the use of the sugar-containing liquid medium obtainable in accordance with the invention in a fermentative production of
 mono-, di- and tricarboxylic acids, in particular aliphatic mono- and dicarboxylic acids having 2 to 10 carbon atoms, such as acetic acid, propionic acid, fumaric acid and succinic acid;
 aliphatic hydroxycarboxylic acids having 3 to 10 carbon atoms, such as lactic acid;
 long-chain alkanols as mentioned above, in particular alkanols having 4 to 10 carbon atoms, such as butanol;
 diols as mentioned above, in particular alkanediols having 3 to 10 and in particular 3 to 8 carbon atoms, such as propanediol;
 ketones as mentioned above, in particular ketones having 3 to 10 carbon atoms, such as acetone;
 amines, in particular aliphatic diamines having 3 to 10 carbon atoms, such as 1,5-diaminopentane;
 nucleotides such as 5'-IMP and 5'-GMP, and
 carbohydrates as mentioned above, in particular disaccharides such as trehalose, oligosaccharides and polysaccharides such as glucan.

In a further especially preferred embodiment, the metabolite produced by the microorganisms in the fermentation takes the form of polyhydroxyalkanoates such as poly-3-hydroxybutyrate and copolyesters with other organic hydroxycarboxylic acids such as 3-hydroxyvaleric acid, 4-hydroxybutyric acid and others described in Steinbüchel (loc. cit.), for example also long-chain (also referred to as longer-chain) hydroxycarboxylic acids such as 3-hydroxyoctanoic acid, 3-hydroxydecanoic acid and 3-hydroxytetradecanoic acid, and mixtures of these. To carry out the fermentation, analogous conditions and procedures as have been described for other carbon sources, for example in S. Y. Lee, Plastic Bacteria Progress and prospects for polyhydroxyalkanoate production in bacteria, Tibtech, vol. 14, (1996), p. 431-438 may be employed here.

In a preferred embodiment, the microorganisms employed in the fermentation are therefore selected from among natural or recombinant microorganisms which overproduce at least one of the following metabolites:
 enzymes such as phytase, xylanase or glucanase;
 amino acids such as lysine, threonine, glutamate or methionine;
 vitamins such as pantothenic acid and riboflavin; precursors and/or derivatives thereof;
 disaccharides such as trehalose;
 polysaccharides such as glucan;
 aliphatic mono- and dicarboxylic acids having 3 to 10 carbon atoms such as propionic acid, fumaric acid and succinic acid;
 aliphatic hydroxycarboxylic acids having 3 to 10 carbon atoms, such as lactic acid;
 polyhydroxyalkanoates such as poly-3-hydroxybutyrate and copolyesters of 3-hydroxybutyric acid;
 ketones having 3 to 10 carbon atoms, such as acetone;

amines, in particular aliphatic diamines having 3 to 10 carbon atoms, such as 1,5-diaminopentane;

alkanols having 4 to 10 carbon atoms, such as butanol; and alkanediols having 3 to 8 carbon atoms, such as propanediol.

Suitable microorganisms are usually selected from among the genera *Corynebacterium, Brevibacterium, Bacillus, Ashbya, Escherichia, Aspergillus, Alcaligenes, Actinobacillus, Anaerobiospirillum, Lactobacillus, Propionibacterium, Rhizopus, Clostridium, Schizophyllum* and *Sclerotium*, in particular from among strains of *Corynebacterium glutamicum, Corynebacterium* sp AJ-1526, *Brevibacterium ammoniagenes, Bacillus subtilis, Bacillus megaterium, Ashbya gossypii, Escherichia coli, Aspergillus niger, Aspergillus terreus, Aspergillus itaconicus, Alcaligenes latus, Anaerobiospirillum succiniproducens, Actinobacillus succinogenes, Lactobacillus delbrückii, Lactobacillus leichmannii, Propionibacterium arabinosum, Propionibacterium schermanii, Propionibacterium freudenreichii, Clostridium propionicum, Clostridium formicoaceticum, Clostridium acetobutylicum, Rhizopus arrhizus, Rhizopus oryzae, Schizophyllum commune* and *Sclerotium rolfsii*.

In a preferred embodiment, the microorganism employed in the fermentation is a strain from the genus *Corynebacterium*, in particular a strain of *Corynebacterium glutamicum*. In particular, it is a strain of the genus *Corynebacterium*, specifically of *Corynebacterium glutamicum*, which overproduces an amino acid, specifically lysine, methionine or glutamate.

In a further preferred embodiment, the microorganism employed in the fermentation is a strain from the genus *Escherichia*, in particular a strain of *Escherichia coli*. In particular, it is a strain of the genus *Escherichia*, specifically of *Escherichia coli*, which overproduces an amino acid, specifically lysine, methionine or threonine.

In a specific preferred embodiment, the metabolite produced by the microorganisms in the fermentation is lysine. To carry out the fermentation, analogous conditions and procedures as have been described for other carbon sources, for example in Pfefferle et al., loc. cit., and U.S. Pat. No. 3,708,395, may be employed here. In principle, both a continuous and a discontinuous (batch or fed-batch) mode of operation are suitable, with the fed-batch mode of operation being preferred.

In a further especially preferred embodiment, the metabolite produced by the microorganisms in the fermentation is methionine. To carry out the fermentation, analogous conditions and procedures as have been described for other carbon sources, for example in WO 03/087386 and WO 03/100072, may be employed here. In the case of the production of lysine, a medium for the fermentation of lysine is produced from the glucose solution obtained in step c) together with nutrient salts and complex nutrient media components, for example molasses. This medium can be sterilized indirectly or directly by steam. After the sterilization, the medium is employed in a fermentation for the production of lysine using customary microorganisms, for example *Corynebacterium glutamicum*. After the fermentation has ended, the fermentation liquor comprises, besides lysine, also the microorganism (biomass), dissolved components of the nutrient medium and, if appropriate, also nonstarchy solid constituents of the starch source which have not been separated completely by the solid/liquid separation (see Chapter 2.2.3). Lysine can be obtained in the customary manner, and this is illustrated in greater detail hereinbelow.

In a further especially preferred embodiment, the metabolite produced by the microorganisms in the fermentation is pantothenic acid. To carry out the fermentation, analogous conditions and procedures as have been described for other carbon sources, for example in WO 01/021772, may be employed here.

In a further especially preferred embodiment, the metabolite produced by the microorganisms in the fermentation is riboflavin. To carry out the fermentation, analogous conditions and procedures as have been described for other carbon sources, for example in WO 01/011052, DE 19840709. WO 98/29539, EP 1186664 and Fujioka, K.: New biotechnology for riboflavin (vitamin B2) and character of this riboflavin. Fragrance Journal (2003), 31(3), 44-48, may be employed here.

In a further especially preferred embodiment, the metabolite produced by the microorganisms in the fermentation is fumaric acid. To carry out the fermentation, analogous conditions and procedures as have been described for other carbon sources, for example in Rhodes et al., Production of Fumaric Acid in 20-L Fermenters, Applied Microbiology, 1962, 10 (1), 9-15, may be employed here.

In a further especially preferred embodiment, the metabolite produced by the microorganisms in the fermentation is lactic acid. To carry out the fermentation, analogous conditions and procedures as have been described for other carbon sources, for example in Narayanan et al., Electronic J. Biotechnol. 2004, 7, http://www.ejbiotechnology.info/content/vol7/issue2/full/7/pdf, may be employed here.

In a further especially preferred embodiment, the metabolite produced by the microorganisms in the fermentation is succinic acid. To carry out the fermentation, analogous conditions and procedures as have been described for other carbon sources, for example in Int. J. Syst. Bacteriol. 26, 498-504 (1976); EP 249773 (1987), Inventors: Lemme and Dana; U.S. Pat. No. 5,504,004 (1996), Inventors: Guettler, Jain and Soni; Arch. Microbiol. 167, 332-342 (1997); Guettler MV. Rumler D, Jain M K., *Actinobacillus succinogenes* sp. nov., a novel succinic-acid-producing strain from the bovine rumen. Int J Syst Bacteriol. 1999 January; 49 Pt 1:207-16; U.S. Pat. No. 5,723,322, U.S. Pat. No. 5,573,931, U.S. Pat. No. 5,521,075, WO99/06532, U.S. Pat. No. 5,869,301 or U.S. Pat. No. 5,770,435, may be employed here.

In a further especially preferred embodiment, the metabolite produced by the microorganisms in the fermentation is itaconic acid. To carry out the fermentation, analogous conditions and procedures as have been described for other carbon sources, for example in Kautola, H., Appl. Microb. Biotechnol., 1990, 33, 7 and Willke et al., Appl. Microbiol. Biotechnol., 2001, 56, 289, may be employed here.

In a further especially preferred embodiment, the metabolite produced by the microorganisms in the fermentation is a phytase. To carry out the fermentation, analogous conditions and procedures as have been described for other carbon sources, for example in WO 98/55599, may be employed here.

In a further especially preferred embodiment, the metabolite produced by the microorganisms in the fermentation is glucan. To carry out the fermentation, analogous conditions and procedures as have been described for other carbon sources, for example in Schilling et al.: Repression of oxalic acid biosynthesis in the unsterile scleroglucan production process with *Sclerotium rolfsii* ATCC 15205, Bioprocess Engineering 22 (2000), 51-55 or Rau et al.: Oxygen controlled batch cultivations of *Schizophyllum commune* for enhanced production of branched β-1,3-glucans, Bioprocess Engineering 11 (1994), 161-165, may be employed here.

In a further especially preferred embodiment, the metabolites produced by the microorganisms in the fermentation are nucleotides such as 5'-IMP and 5'-GMP. To carry out the fermentations, analogous conditions and procedures as have been described for other carbon sources, for example in Sato et al., Accumulation of Guanosine Polyphosphates by *Brevibacterium* ammoniagenes: Isolation and Identification of the Products. Agr. Biol. Chem. 40 (3), 1976, 465-474; Mori et al: A novel process of inosine 5'-monophosphate production using overexpressed guanosine/inosine kinase. Appl. Microbiol. Biotechnol. (1997) 48: 693-698, or GB 01188885, may be employed here.

In a further especially preferred embodiment, the metabolite produced by the microorganisms in the fermentation is glutamate. To carry out the fermentations, analogous conditions and procedures as have been described for other carbon sources, for example in E. Kimura, L-Glutamate Production, in: Handbook of *Corynebacterium glutamicum*, CRC press, Boca Raton, Fla., 439-464, may be employed here.

In a further especially preferred embodiment, the metabolite produced by the microorganisms in the fermentation is 1,5-diaminopentane. To carry out the fermentations, analogous conditions and procedures as have been described for other carbon sources, for example in JP 2004222569, may be employed here.

In a further especially preferred embodiment, the metabolite produced by the microorganisms in the fermentation is 5-ketogluconic acid. To carry out the fermentation, analogous conditions and procedures as have been described for other carbon sources, for example in Elfari, M. et al., Appl. Microbiol. Biotechnol. 2005, 66, 668, and Herrmann U., et al., Appl. Microbiol. Biotechnol. 2004, 64, 86, may be employed here.

In a further especially preferred embodiment, the metabolite produced by the microorganisms in the fermentation is 2,5-diketogluconic acid. To carry out the reaction, analogous conditions and procedures as have been described for other carbon sources, for example in Roper, H., Starch-Starke 1990, 42, 342 or Zelic, B. et al., Chem. Biochem. Eng. Q. 2002, 16, 7, may be employed here.

Work-Up of the Fermentation

The process according to the invention for the production of an organic substance by fermentation results in a fermentation liquor which, besides the desired metabolite, comprises essentially the biomass generated during the fermentation and sugars which have not been utilized, as well as buffer salts and nutrient salts which have not been utilized. As a rule, the fermentation is therefore followed by a further processing of the fermentation liquor in order to obtain the product of value, i.e. the organic substance produced by the fermentation process, and to convert it into a manageable form, or a marketable form, and in order to either dispose of, or further utilize, the secondary products generated in the fermentation, such as biomass and the aqueous constituents.

The type of work-up, and the steps required therefor, depend in a manner known per se on the properties of the substances in the fermentation liquor, and, in particular, on the nature of the metabolite produced.

Typically, work-up processes contain one or more of the following steps, which may be combined in any desired sequence and specification:

deactivation of the microorganism, for example by sterilization in the manner described above;
separation of the biomass from the fermentation liquor;
isolation of the nonvolatile metabolite from the fermentation liquor which still comprises biomass, or from which the biomass has already been separated off;
purification of the desired metabolite;
concentration of the metabolite;
concentration of the biomass.

Not all of the steps have to be mandatory constituents of the work-up process. For example, an additional purification of the metabolite(s) can be dispensed with if the purity of the product does not have to meet high requirements.

The separation of the biomass from the fermentation liquor is carried out by customary processes of solid/liquid phase separation (for example described in Belter, P. A, Bioseparations: Downstream Processing for Biotechnology, John Wiley & Sons (1988), and Ullmann's Encyclopedia of Industrial Chemistry, 5th edition on CD-ROM, Wiley-VCH), and is, as a rule, carried out by mechanical processes such as decanting, separation, floatation, centrifugation, sedimentation, filtration or membrane processes. Multi-step combinations of a process, or combinations of different processes, such as, for example, decanting and separation, are also feasible. Moreover, it is also possible to employ wash water in order to increase the yield of the nonvolatile metabolite when the biomass is separated off. The abovementioned processes are preferably employed when the metabolite is a substance which is present in the fermentation liquor in the dissolved state. In the case of oily or solid metabolites, a mechanical separation by means of decanting, separation, floatation, centrifugation, sedimentation is, as a rule, meaningful when there are density differences between the biomass and the metabolite. Otherwise, it is in particular chromatographic processes, distillation processes or extraction processes which are suitable here.

The isolation, or depletion, of the product of value from the fermentation liquor is, as a rule, carried out in such a way that at least one product of value is depleted or isolated from the fermentation liquor in such a way that the content of this product of value in the remaining fermentation liquor amounts to no more than 20% by weight, in particular no more than 10% by weight, specifically no more than 5% by weight and very specifically no more than 2.5% by weight, in each case based on the total weight of the remaining fermentation liquor. The isolation or depletion of the product of value from the fermentation liquor can be effected in one or more steps.

To isolate a product of value which is dissolved in the fermentation liquor, a procedure will advantageously be followed in which the biomass and other undissolved constituents are first removed from the fermentation liquor, for example by means of centrifugation or filtration, and the product of value is subsequently isolated from the liquid phase, for example by crystallization, precipitation, adsorption, distillation, chromatography, extraction, ion exchange, membrane processes (preferably diffusion dialysis, electrodialysis, nanofiltration). Alternatively, the product of value can also be isolated directly from the fermentation liquor, for example by the use of chromatographic processes, extraction processes, membrane processes, adsorption processes and distillation. A chromatographic process which is to be mentioned in particular is ion-exchange chromatography, where the product of value can be isolated selectively on the chromatography column.

To separate off the product of value, it may be meaningful chemically to modify the product of value in a first step in the fermentation liquor, for example by esterification or salt formation, in order to thereby improve its separation characteristics.

Crystallization is a process which makes possible both a separation of the product of value from the fermentation liquor and a further purification of the product of value. In this case, it is preferably employed in combination with a mechanical separation, as already mentioned above, in which the crystals can be separated from the mother liquor.

In the case of volatile or oily compounds, checking the maximum temperatures during the work-up, in particular during drying, is, as a rule, necessary. These compounds can advantageously also be isolated by formulating them in quasi-solid form (pseudo-solid form) on adsorbents. Adsorbents which are suitable for this purpose are detailed for example in WO 2005/116228, which has been granted to the applicant company, for example active charcoals, aluminas, silica gels, silicic acid, clay, carbon blacks, zeolites, inorganic alkali and alkaline earth metal salts such as the hydroxides, carbonates, silicates, sulfates and phosphates of sodium, potassium, magnesium and calcium, in particular magnesium and calcium salts, for example $Mg(OH)_2$, $MgCO_3$, $MgSiO_4$, $CaSO_4$, $CaCO_3$, alkaline earth metal oxides, for example MgO and CaO, other inorganic phosphates and sulfates, for example $ZnSO_4$, salts of organic acids, in particular their alkali and alkaline earth metal salts, and specifically their sodium and potassium salts, for example sodium acetate, sodium formate, sodium hydrogen formates, sodium citrate, potassium acetate, potassium formate, potassium hydrogen formates and potassium citrate, higher-molecular-weight organic carriers such as optionally modified starches, cellulose, lignin, the carriers mentioned hereinbelow in connection with the product formulation, and the maize gluten according to the invention. Examples of products of value which can be isolated advantageously in this manner are γ-linolenic acid, dihomo-γ-linolenic acid, arachidonic acid, eicosapentaenoic acid and docosahexaenoic acid, furthermore propionic acid, lactic acid, propanediol, butanol and acetone. Again, these compounds in pseudo-solid formulation are understood as meaning, for the purposes of the present invention, nonvolatile metabolites or products of value in solid form.

The abovementioned process steps of the work-up may, in some cases, require the use of additives (for example for the regeneration of the ion exchanger, the solvent for the extraction and the like), and/or a stream of secondary products can be generated in some cases (for example mother liquor of the crystallization, eluate of the ion exchanger). These streams of secondary products, which in some cases may still comprise the product of value, the biomass, nonstarchy solid constituents of the maize employed as the starch source, and components of the additives, can either be worked up further, in some cases recirculated to any process step in the overall process, disposed of, or reused.

All of the abovementioned streams, preferably the biomass-containing streams, the streams comprising product of value and the product streams, comprise, under certain circumstances, high water concentrations (as the result of the fermentation or wash water in the work-up) and may be concentrated (reduction of the water content). This can be effected thermally, for example by means of evaporation, drying, or mechanically by means of membrane processes, filtration and the like. The water can be disposed of or recirculated as process water and employed for example for slurrying the endosperm fraction or for slurrying the separated solid in the case of the multi-step separation of the maize gluten.

A further specific embodiment relates to a process in which most or all of the volatile constituents of the fermentation liquor are removed without previously isolating or depleting the product of value, and, if appropriate, without previously separating off the biomass, a solid formulation of the product of value being obtained. A more detailed description on carrying out such a process is found in WO 2007/028804, granted to the applicant company, which is herewith incorporated by reference.

The properties of the dried product of value, which is present together with the solid constituents of the fermentation, can be finished in a targeted manner known per se with regard to a variety of parameters such as active substance content, particle size, particle shape, susceptibility to dusting, hygroscopicity, stability, in particular storage stability, color, odor, flowing behavior, susceptibility to agglomerating, electrostatic charging, sensitivity to light and temperature, mechanical stability and redispersibility by adding formulation auxiliaries such as carriers and coating materials, binders and other additives.

The formulation auxiliaries which are conventionally employed include, for example, binders, carriers, powder-coating materials, flow improvers, furthermore color pigments, biocides, dispersants, antifoam agents, viscosity regulators, acids, bases, antioxidants, stabilizers for enzymes, enzyme inhibitors, adsorbates, fats, fatty acids, oils or mixtures of these. Such formulation auxiliarys are advantageously employed as drying auxiliaries in particular when using formulation and drying methods such as spray drying, fluidized-bed drying and lyophilization. As regards further details, reference is made to WO 2007/028804.

The amount of the abovementioned additives, and, if appropriate, further additives such as coating materials can vary greatly, depending on the specific requirements of the product of value in question and as a function of the properties of the additives employed and can be for example in the range of from 0.1 to 80% by weight and in particular in the range of from 1 to 30% by weight, in each case based on the total weight of the product, or substance mixture, in readily formulated form.

Formulation auxiliaries can be added before, during or after the work-up of the fermentation liquor (also referred to as product formulation or solids design), in particular during drying. An addition of formulation auxiliarys prior to the work-up of the fermentation liquor or the product of value can be particularly advantageous in order to improve the processability of the substances, or products, to be worked up. The formulation auxiliaries can be added both to the product of value obtained in solid form and to a solution or suspension comprising this product, for example directly to the fermentation liquor after the fermentation has ended, or to a solution or suspension obtained in the course of the work-up before the final drying step.

Thus, the auxiliaries can be admixed for example to a suspension of the product of value; such a suspension can also be placed on a carrier material, for example by spraying on or admixing. The addition of formulation auxiliaries during drying may play a role for example when a solution or suspension comprising the product of value is sprayed. Formulation auxiliaries are added in particular after drying, for example when applying coatings or coating layers to dried particles. Further auxiliaries may be added to the product, both after drying and after any coating step which may have been carried out.

The volatile constituents are removed from the fermentation liquor in a manner known per se by customary methods for separating solid phases from liquid phases, including filtration processes and processes for evaporating volatile constituents of the liquid phases. Such processes, which may also comprise steps for the initial purification of the products of value, and also finishing steps, are described, for example, in Belter, P. A, Bioseparations: Downstream Processing for Biotechnology, John Wiley & Sons (1988), and Ullmann's Encyclopedia of Industrial Chemistry, 5th edition on CD- ROM, Wiley-VCH. Processes, apparatuses, auxiliaries and general and specific embodiments which can be used within the scope of product formulation or the work-up after the fermentation has ended and which are known to the skilled worker are described, furthermore, in EP 1038 527, EP 0648 076, EP 835613, EP 0219 276, EP 0394 022, EP 0547 422, EP 1088 486, WO 98/55599, EP 0758 018 and WO 92/12645.

In a first variant of this embodiment, the nonvolatile product of value, as long as it is present in dissolved form in the liquid phase, will be converted from the liquid phase into the solid phase, for example by crystallization or precipitation. This is followed by a separation of the nonvolatile solid constituents including the product of value, for example by means of centrifugation, decanting or filtration. In a similar manner, it is also possible to separate off oily products of value, where the respective oily fermentation products are converted into a solid form by addition of adsorbents, for example silica, silica gels, lehm, clay and active charcoal.

In a second variant of this embodiment, the volatile constituents are removed by evaporation. Evaporation can be effected in a manner known per se. Examples of suitable processes for evaporating volatile constituents are spray drying, fluidized-bed drying or agglomeration, lyophilization, drying in flow and contact dryers, and extrusion drying. A combination of the abovementioned processes with shaping processes such as extrusion, pelleting or prilling may also be carried out. In the case of the last-mentioned processes, it is preferred to employ partially or largely predried substance mixtures which contain product of value.

In a preferred embodiment, the removal of the volatile constituents of the fermentation liquor comprises a spray-drying process or a fluidized-bed drying process, including fluidized-bed granulation. To this end, the fermentation liquor, if appropriate after a preceding separation step for removing coarse solid particles which comprise no, or only small amounts of, nonvolatile product of value, will be conveyed to one or more spray-drying or fluidized-bed drying apparatuses. The transport, or the conveying, of the solids-loaded fermentation liquor is expediently performed by means of conventional transport devices for solid-containing fluids, for example pumps, such as eccentric screw pumps (for example from Delasco PCM) or high-pressure pumps (for example from LEWA Herbert Ott GmbH).

In the specific case of lysine production, the work-up process comprises a separation of the biomass by separators. The biomass-containing fraction is then dried in a drum dryer or tubular bundle dryer. If appropriate, a fermentation residue of the vitamin $B_2$ fermentation, known as "BFR" (vitamin $B_2$ fermentation residues) is admixed to the biomass-containing fraction prior to drying. The low-solid fraction is acidified and passed over an ion exchanger. The lysine is bound to this ion exchanger. The lysine-depleted fermentation liquor which leaves the ion exchanger is concentrated by evaporating water; solids which crystallize in the process are separated off and dried. The resulting product is termed "fertilizer" and can be recirculated into the process or employed as fertilizer and/or for further applications. The mother liquor of the crystallization, known as "CMS" (Condensed Molasses Solubles), is recirculated. The lysine which is bound to the ion exchanger is eluted with ammonia water and concentrated by evaporating water. Lysine can be obtained from this concentrated liquor as the free base in the form of a liquid formulation. In the next process step, the lysine is crystallized in the form of lysine hydrochloride by addition of hydrochloric acid. The crystals are separated by centrifugation and dried. The mother liquor of the crystallization is either recirculated to the eluate of the ion exchanger or can be withdrawn as lysine in liquid formulation.

As an alternative to the above-described work-up, the lysine-containing fermentation liquor is directly spray-dried after the fermentation. Optionally, the fermentation residue from the vitamin $B_2$ production may be added. A preceding one- or multi-step evaporation of the fermentation liquor, which is possible, may lead to reduced energy costs and investments.

Use of the Glucose in a Nonfermentative Reaction

A further preferred subject matter of the invention is the use of the glucose solution which is obtainable in accordance with the invention as a glucose source for the nonfermentative production of an organic substance as defined above.

Accordingly, a further subject matter of the invention is a process for the production of an organic substance by nonfermentative reaction, comprising the following steps:

i. Providing an aqueous glucose solution according to the invention, for example by producing the glucose solution in accordance with the process according to the invention, and ii. Using the glucose solution or an essentially anhydrous glucose obtained by concentrating the solution (water content <10% by weight), in a nonfermentative reaction for the production of the desired organic substance.

The nonfermentative reaction can be carried out in the customary manner known to the skilled worker. To this end, the aqueous glucose produced in accordance with the invention will, as a rule, be reacted, if appropriate using a catalyst.

In an especially preferred embodiment, the organic substance which can be prepared from glucose via the nonfermentative route is 5-hydroxymethylfurfural. To carry out the reaction, analogous conditions and procedures as have been described for other carbon sources, for example in Cottier et al., Trends Heterocycl. Chem. 1991, 2, 233; Lewkowski, J., Arkivoc 2001, 2, 17; Kuster, B. F. M. et al., Carbohydr. Res. 1977, 54, 159, EP 0230250, FR 2464260 or DE 3601281, may be employed here.

In a further, especially preferred embodiment, the organic substance which can be prepared from glucose via the nonfermentative route is laevulic acid. To carry out the reaction, analogous conditions and procedures as have been described for other carbon sources, for example in Horvat et al, Tetrahedron Lett. 1985, 26, 2111 or U.S. Pat. No. 3,258,481, may be employed here.

In a further, especially preferred embodiment, the organic substance which can be prepared from glucose via the nonfermentative route is gluconic acid. To carry out the reaction, analogous conditions and procedures as have been described for other carbon sources, for example in Lichtenthaler, F. W., Acc. Chem. Res. 2002, 35, 728, Besson, M. et al., J. Catal. 1995, 152, 116 or EP 233816, may be employed be here.

In a further, especially preferred embodiment, the organic substance which can be prepared from glucose via the nonfermentative route is glucuronic acid. To carry out the reaction, analogous conditions and procedures as have been described for other carbon sources, for example in Corma, A. et al., Chemical Routes for the Transformation of Biomass into Chemicals., Chem. Rev. 2007, 107, 2411-2502, may be employed here.

In a further, especially preferred embodiment, the organic substance which can be prepared from glucose via the nonfermentative route is 2-ketogluconic acid. To carry out the reaction, analogous conditions and procedures as have been described for other carbon sources, for example in US 2002177198, WO 9915673 or EP 867446, may be employed here.

In a further, especially preferred embodiment, the organic substance which can be prepared from glucose via the non-fermentative route is glutaric acid. To carry out the reaction, analogous conditions and procedures as have been described for other carbon sources, for example in Besson, M. et al., Recl. Tray. Chim. Pys-Bas 1996, 115, 217 and Dirkx, J. M. H. et al., J. Catal. 1981, 67, 1, may be employed here.

In a further, especially preferred embodiment, the organic substance which can be prepared from glucose via the non-fermentative route is sorbitol. To carry out the reaction, analogous conditions and procedures as have been described for other carbon sources, for example in Dechamp, N. et al., Catal. Today 1995, 24, 29 and Maranhao, L. C. A. et al., Ind. Eng. Chem. Res. 2005, 44, 9624, WO 02100537, WO 02100539 and WO 2004052813, may be employed here.

In a further, especially preferred embodiment, the organic substance which can be prepared from glucose via the non-fermentative route is isosorbide. To carry out the reaction, analogous conditions and procedures as have been described for other carbon sources, for example in WO 9804540, WO 9200947 and U.S. Pat. No. 4,297,290, may be employed here.

In a further, especially preferred embodiment, the organic substance which can be prepared from glucose via the non-fermentative route is alkylpolyglucosides. To carry out the reaction, analogous conditions and procedures as have been described for other carbon sources, for example in U.S. Pat. No. 5,480,979 and U.S. Pat. No. 5,698,684, may be employed here.

In a further, especially preferred embodiment, the organic substance which can be prepared from glucose via the non-fermentative route is HFCS (High-Fructose Corn Syrup). To carry out the reaction, analogous conditions and procedures as have been described for other carbon sources, for example in Marshall et al., Enzymatic Conversion of d-Glucose to d-Fructose 1957, Science 125 (3249), 648 and U.S. Pat. No. 4,523,960, may be employed here.

Formulation of the Secondary Products

As has already been explained above, not only steps a) and c) of the process according to the invention for producing glucose, but also the fermentative further processing of the glucose to give products of value, generate a series of substance streams as secondary products or coupled products. As a rule, these are one or more of the following substance streams, preferably in the amounts detailed:

- dust-like fines of the maize cleaning process, if generated, typically in an amount of up to 5% by weight, in particular 0.1 to 3% by weight;
- maize bran, if generated, typically in an amount of up to 7% by weight, for example 1 to 6% by weight;
- maize germ, typically in an amount of from 2 to 16% by weight, preferably 4 to 12% by weight;
- maize gluten, typically in an amount of from 4 to 40% by weight, preferably 8 to 30% by weight;
- biomass, typically in an amount of from 1 to 40% by weight, preferably 5 to 20% by weight and
- if appropriate, secondary product streams which may be generated in the work-up process of the product of value, if generated, typically in an amount of up to 100% by weight, preferably 0.2 to 50% by weight, especially preferably 0.3 to 20% by weight, where all percentages by weight are based on the total weight of the maize employed for the glucose production.

These substance streams can be processed separately or can be disposed of. It is also possible to mix these substance streams as desired, i.e. some or all of them, in any desired combination, for the purposes of further processing (i.e. combining at least two substance streams). As a rule, the further processing is preceded by a drying step, where, if appropriate, the substance streams to be mixed with one another are dried before mixing or after mixing. Frequently, a procedure will be followed in which the solid particles of the substance streams which have been freed from at least some of the water are agglomerated or jointly milled.

The process steps drying, agglomerating and milling can be carried out, and combined, optionally and in any desired sequence relative to the mixing of the different streams. Preferably, a procedure will be followed in which the mixing of the substance streams gives a secondary product which is preferably suitable as a feedstuff and which comprises at least a portion of the substance streams from the maize processing (or sugar production) and comprises at least one constituent from the work-up of the fermentation liquor (biomass or secondary product streams).

If appropriate, formulation auxiliaries, active substances or one or more biomasses or one or more secondary product streams of other fermentation processes may be added to the secondary products thus produced, it being possible to carry out this addition at any point of the process.

In the undried state, the residual moisture contents of these secondary products amount to 10 to 90% by weight, preferably 40 to 80% by weight. In the dried state, the residual moisture contents of the secondary products amount to 1 to 20% by weight and preferably 3 to 18% by weight and especially preferably 5 to 15% by weight.

The mean particle diameter of the solids content of the secondary products is between 50 am and 8 mm, preferably between 100 μm and 5 mm and especially preferably between 150 μm and 3 mm.

If a secondary product is a mixture of different solids fractions, the particle size distributions of the individual substance streams of which the secondary product is composed will, prior to mixing, generally be selected or adjusted such that a separation of the substance streams does not occur, or is at least kept to a minimum. As a rule, this is ensured when the substance streams to be mixed have a particle size which is as similar as possible, or when the so-called SPAN value of the secondary product mixture is less than 4, preferably less than 3, especially preferably less than 2 and in particular less than 1.8. In this context, the SPAN value of the secondary product mixture is defined as $$SPAN=(D_{90}-D_{10})/D_{50}$$

Here, the $D_{50}$ value is the weight-average particle diameter of the secondary product mixture, i.e., based on the weight, the $D_{50}$ value indicates the particle diameter which is exceeded by 50% by weight of the particles and not reached by 50% by weight. The $D_{90}$ value is the diameter which 90% by weight of the particles do not reach, or which is exceeded by 10% by weight. The $D_{10}$ value is the diameter which 10% by weight of the particles do not reach, or which is exceeded by 90% by weight. The SPAN value, or the particle diameters and their distribution, can be determined in a manner known per se, for example by screen analysis or by light diffraction.

If a secondary product is produced from at least one dry substance stream and at least one liquid stream, it is possible on the one hand to dry the liquid substance streams and then to treat them like solid substance streams (see above). As regards the mixing of these substance streams, what has been said for the mixture of the substance streams which are already dry in their original state also applies here. On the other hand, it is also possible to mix the liquid and the dry substance streams with one another before or during drying. The advantage is that the solid comprised in the liquid or suspended substance stream is thoroughly intermixed with, and distributed in, the dry substance streams, or the liquid substance stream is applied as a coating to the solid constituents of the dry substance streams, or the liquid substance streams are utilized for agglomerating, or binding, the solid particles of the dry substance stream.

In one embodiment of the invention, the dusty fines are discarded and not intermixed with the secondary products.

In one embodiment of the invention, the maize bran is not intermixed with the secondary products, but utilized as a stand-alone product.

In one embodiment of the invention, the maize germ is not intermixed with the secondary products, but utilized as a stand-alone product, for example for obtaining corn oil.

In one embodiment of the invention, the maize gluten is not intermixed with the secondary products, but utilized as a stand-alone product.

In one embodiment of the invention, the biomass is not intermixed with the secondary products, but utilized as a stand-alone product.

In one embodiment of the invention, the secondary product streams are not intermixed with the secondary products, but utilized as stand-alone products in their own right, or discarded or disposed of.

In a particular embodiment of the invention, a portion or the total amount of the maize bran generated, for example 10 to 100% by weight, based on the dry-matter content of the maize bran which has been generated in total, is mixed with at least one secondary product stream, for example with 10 to 100% by weight, based on the respective secondary product stream, and dried in order to give a secondary product which comprises maize bran. Optionally, the maize bran may be milled before mixing, so that mean particle sizes of 150 to 1400 µm and especially preferably 200 µm to 800 µm, are obtained. A further option consists in adding, to the maize bran, a portion of the dusty maize fines generated, for example 10 to 100% by weight, before or after milling.

A process for the fermentative production of lysine generates for example a syrup-like secondary product stream CMS with a dry-matter content of 40 to 90% by weight, which can be admixed or combined with the maize bran, for example by means of spraying on, and the substances can then be dried together. After drying, the agglomerates which may have formed can optionally be comminuted. The composition (based on the dry matter) of the secondary product obtained in this manner is, as a rule, as follows:

Crude protein: 5 to 60% by weight, preferably 10 to 50% by weight
Starch: 1 to 50% by weight, preferably 5 to 40% by weight
Crude fiber: 1 to 20% by weight, preferably 2 to 10% by weight
Crude fat: 1 to 20% by weight, preferably 1 to 10% by weight
Crude ash: 0 to 15% by weight, preferably 0.1 to 7% by weight
Lysine: 0 to 10% by weight, preferably 0 to 5% by weight In a further, especially preferred embodiment of the invention, a secondary product A is produced in which in each case 0 to 100% by weight, preferably 30 to 100% by weight, especially preferably all of the maize germ generated, 10 to 100% by weight, preferably 30 to 100% by weight, especially preferably all of the maize gluten generated, and 10 to 100% by weight, preferably 30 to 100% by weight, especially preferably all of the biomass generated, are mixed with one another. This secondary product can optionally comprise a fraction of from 0 to 100% of the maize bran generated and 0 to 100% of the fines.

The following process variants are possible to produce this secondary product A.

In a first variant, all the streams (maize germ, maize gluten, biomass and, optionally, maize bran and/or fines) are mixed and dried. If appropriate, the dry secondary product or the dry starting materials maize germ and maize bran can additionally be milled, so that a mean particle size and a residual moisture as described above can be obtained. In a second variant, only the moist streams of the maize gluten and of the biomass are first mixed with one another and then dried jointly. The advantage here is that the maize germ, which is already dry, and, optionally, also the dry maize bran do not have to be passed unnecessarily through the dryer. After the components have been dried, it is possible either to directly mix all the streams or first to mill, and then mix, the individual streams. After mixing, a further milling step may follow. A mean particle size and a residual moisture as described above can be obtained. In a third variant, the two moist streams of the biomass and of the maize gluten are initially dried separately. This can have the advantage that undesired decomposition reactions, such as, for example, a Maillard reaction between sugar and protein components which may be present in the streams, are avoided or reduced. The dry streams of the maize gluten, of the biomass, of the maize germ and optionally of the maize bran can optionally be milled and mixed, or else the mixing step may be followed by an optional milling step. A mean particle size and a residual moisture as described above can be obtained. In a fourth variant, 10 to 100% of at least one solid stream generated is combined with at least one stream to be dried, either during or before drying. The advantage here is that desired agglomerates may be formed, that the flow behavior of the product is improved or that the tendency of the product to dust is reduced. Thus, for example, the maize gluten (or parts thereof) which is generated in moist form may be mixed, before or during drying, with portions of maize bran (optionally milled), with portions of maize germ (optionally milled) or with portions of fines, or with any combinations thereof. It is also possible to mix, before or during the drying, the biomass (or portions thereof) which is obtained in moist form with portions of maize bran (optionally milled), with portions of maize germ (optionally milled) or with portions of fines, or any combinations thereof.

In a specific embodiment of the invention, biomass from the lysine fermentation is used when producing the secondary product A. The streams maize gluten, maize germ and biomass are used in an amount of in each case 50 to 100% by weight, based on the total amount of the stream generated in each case, and processed by the above-described processes to give a secondary product. This secondary product is novel and also subject matter of the invention. The preferred composition (based on the dry matter) of the secondary product is, as a rule, as follows:

Crude protein: 10 to 60% by weight, particularly preferably 20 to 50% by weight
Total sugars: 0.1 to 50% by weight, particularly preferably 5 to 45% by weight
Crude fibers: 0 to 10% by weight, particularly preferably 0 to 7% by weight
Crude fat: 1 to 30% by weight, particularly preferably 5 to 20% by weight
Crude ash: 0 to 15% by weight, particularly preferably 0.1 to 7% by weight
Lysine: 0.1 to 20% by weight, particularly preferably 0.2 to 10% by weight.

In a further embodiment of the production of the secondary product A, the biomasses of different fermentations are mixed. Thus, the different biomasses can, again, be first dried separately from one another or else mixed and then dried jointly. The biomasses can be mixed with each other in any mixing ratio desired. Preferably, 30 to 100% and more preferably 50 to 100%, of the biomass generated in a respective fermentation is mixed with one another here.

In a further embodiment of the invention, at least one biomass from a further fermentation process is added to any (above-described) secondary product at any point of the preparation process. In a particular embodiment, it is a secondary product which comprises both biomass from a lysine fermentation (as described above) and biomass from a $B_2$ fermentation (BFR, as defined above). Preferably, 30 to 100% and more preferably 50 to 100%, of the biomass generated in a respective fermentation is mixed with one another here. If appropriate, the secondary product comprises amounts of from 50 to 100% of the maize germ generated and/or 50 to 100% of the maize gluten generated and/or 50 to 100% of the maize bran generated, and 0 to 100% of the fines generated.

In a further embodiment, it is a secondary product which comprises both biomass from a chemical fermentation such as, for example, a lysine fermentation or a glutamate fermentation, and biomass from a bioethanol fermentation.

When mixing the at least two biomasses, in a particular embodiment of the invention they are biomasses from fermentations which are in each case operated with a glucose stream obtained from the maize starch saccharification according to the invention. Here, a procedure may be followed whereby the two fermentations are the same glucose stream. In another embodiment, in each case the glucose streams obtained from processes according to the invention are employed, but they are separately produced glucose streams with, as a rule, different glucose purities. The at least two glucose media here typically differ in the concentration of the nonstarchy solid components. Based on the dry matter, at least one stream with a high and one stream with a low content of nonstarchy, solid components, are generated. The different purities of the glucose streams can be generated by processes such as decanting, separation, centrifugation, sedimentation, filtration or membrane processes. In this context, multi-step combinations of a process, or combinations of different processes, are feasible, such as, for example, decanting and separation.

However, the at least two fermentations may also be based on different carbon sources, with at least one carbon source being a glucose which is obtainable by the process according to the invention.

A secondary product which comprises at least the biomass from two different fermentations may also comprise at least 2 different metabolites.

Analogously to the above-described secondary product A comprising maize gluten, maize germ and biomass (optionally maize bran) and the relevant production process, it is also possible to produce secondary products which comprise, as dry matter, only maize gluten and biomass (optionally maize bran and/or formulation auxiliaries) or else only maize germ and biomass (optionally maize bran and/or formulation auxiliaries) or only maize gluten and maize germ (optionally maize bran and/or formulation auxiliaries). The production processes which are possible are analogous to those mentioned above.

All secondary products may furthermore comprise formulation auxiliaries, inerts, fillers or further active substances which are added to any process step of the production.

The properties of the secondary product can be finished in a targeted manner known per se with regard to a variety of parameters such as particle size, particle shape, susceptibility to dusting, hygroscopicity, stability, in particular storage stability, color, odor, flowing behavior, susceptibility to agglomerating, electrostatic charging, sensitivity to light and temperature, mechanical stability and redispersibility by adding formulation auxiliaries such as carriers and coating materials, binders and other additives.

The formulation auxiliaries which are conventionally employed include, for example, binders, carriers, powder-coating materials/flow improvers, furthermore color pigments, biocides, dispersants, antifoam agents, viscosity regulators, acids, bases, antioxidants, stabilizers for enzymes, enzyme inhibitors, adsorbates, fats, fatty acids, oils or mixtures of these. Such formulation auxiliaries are advantageously employed as drying auxiliaries in particular when using formulation and drying methods such as spray drying, fluidized-bed drying and lyophilization.

Examples of binders are carbohydrates, particularly sugars such as mono-, di-, oligo- and polysaccharides, for example dextrins, trehalose, glucose, glucose syrup, maltose, sucrose, fructose and lactose; colloidal substances such as animal proteins, for example gelatin, casein, in particular sodium caseinate, plant proteins, for example soya protein, pea protein, bean protein, lupin, zein, wheat protein, maize protein and rice protein, synthetic polymers, for example polyethylene glycol, polyvinyl alcohol and in particular the Kollidon brands from BASF, optionally modified biopolymers, for example lignin, chitin, chitosan, polylactide and modified starches, for example octenyl succinate anhydride (OSA); gums, for example acacia gum; cellulose derivatives, for example methylcellulose, ethylcellulose, (hydroxyethyl)methylcellulose (HEMC), (hydroxypropyl)methylcellulose (HPMC), carboxymethylcellulose (CMC); flours, for example maize flour, wheat flour, rye flour, barley flour and rice flour.

Examples of carriers and dietary fibes or fillers are carbohydrates, in particular the sugars which have been mentioned above as binders, and starches, for example maize starch, rice starch, potato starch, wheat starch and cassava starch; modified starches, for example octenyl succinate anhydride; cellulose and microcrystalline cellulose; inorganic minerals or loam, for example clay, coal, kieselguhr, silica, tallow and kaolin; coarse meals, for example coarse wheat meal, bran, for example wheat bran, the flours which have been mentioned above as binders; salts such as metal salts, in particular alkali metal and alkaline earth metal salts of organic acids, for example Mg, Ca, Zn, Na and K citrates, acetates, formates and hydrogen formates, inorganic salts, for example Mg, Ca, Zn, Na and K sulfates, carbonates, silicates or phosphates; alkaline earth metal oxides such as CaO and MgO; inorganic buffers such as alkali metal hydrogen phosphates, in particular sodium and potassium hydrogen phosphates, for example $K_2HPO_4$, $KH_2PO_4$ and $Na_2HPO_4$; and generally the adsorbents mentioned in connection with the production according to the invention of metabolites with a low melting point or of oily consistency. Further fillers or dietary fibers may also be fatty products such as, for example, soya flour, coarse soya meal, or flours and crushed grains of maize, rye, wheat, barley, peas.

Examples of powder-coating materials or flow improvers are kieselguhr, silica, for example the Sipernat brands from Degussa; clay, alumina, sepiolites, kenites, montmorillonites, zeolites, coal, tallow and kaolin; the starches, modified starches, inorganic salts, salts of organic acids and buffers which have been mentioned above as carriers; cellulose and microcrystalline cellulose.

As regards other additives, examples which may be mentioned are color pigments such as $TiO_2$; biocides; dispersants; antifoams; viscosity regulators; inorganic acids such as phosphorus acids, nitric acid, hydrochloric acid, sulfuric acid; organic acids such as saturated or unsaturated mono- and dicarboxylic acids, for example formic acid, acetic acid, propionic acid, butyric acid, valeric acid, palmitic acid, stearic acid, oxalic acid, malonic acid, succinic acid, glutaric acid, adipic acid, pimelic acid, maleic acid and fumaric acid; bases such as alkali metal hydroxides, for example NaOH and KOH; antioxidants; stabilizers for enzymes; enzyme inhibitors; adsorbates, fats; fatty acids and oils.

The amount of the abovementioned additives and, if appropriate, further additives such as coating materials can vary widely depending on the specific requirements of the secondary product in question and depending on the properties of the additives employed, for example in the range of from 0.1 to 80% by weight based on the total weight of the finished, formulated product or composition.

The addition of formulation auxiliaries can be effected at any stage in the production of the secondary product, in particular during drying, which may be required. The formulation auxiliaries can be added both to the secondary product, which is obtained in solid form, and to a solution or suspension comprising said secondary product. In particular after drying, an addition of formulation auxiliaries is effected for example when applying coatings or layers of coatings to dried particles. Further auxiliaries may be added to the product both after drying and after a coating step which may have been carried out.

Further active substances, preferably active substances conventionally used in the feedstuffs industry, may optionally be added to the secondary products at any stage of the production process, in addition to the respective metabolite of the fermentation. Here, active substances are understood as meaning all vitamins (preferably A, B1, B2, B5, B6, C, D3 and E), carotenoids, enzymes (preferably phytase, xylanase, glucanase, amylase, cellulase, hemicellulase, protease, lipase, pectinase, phosphatases), probiotics (for example *Enterococcus* ssp., *Lactobacillus* ssp. *Bacillus* ssp., *Pediococcus* ssp.), antibiotics; organic acids and amino acids (methionine, lysine, etc.). The active substances will preferably amount to from 0.001 to 20% by weight, especially preferably from 0.01 to 5% by weight of the secondary product (based on the dry matter).

The examples which follow are intended to illustrate the invention, but are not to be construed as limiting.

A maize of specification US Yellow No. 2 with a humidity of 11.9% by weight was employed as feedstock in the maize milling experiments. Based on dry matter, this maize comprised 3.8% by weight of crude fat and 75.3% by weight of starch.

EXAMPLE 1

Preparation of a Glucose Solution

Step a): Fractional Milling of Maize
a.1. Precleaning of the Maize

In a first step, the fractions A (particle diameter >12 mm; 0.0% by weight of the maize employed) and fraction B (particle diameter <6.5 mm, 4.05% by weight of the maize employed) were separated off from the bulk of the maize stream (fraction C) by screening. In a further step, light constituents were removed by sifting (0.18% by weight) and were discarded. Fraction C was subsequently freed from stones on a stone sorter, so that the fraction was free of stones.

To optimize the starch yield of the overall process, fraction B was again separated, by screening, into a fraction B1 with particle diameters of between 6.5 and 4.0 mm (2.95% by weight of the maize employed), a fraction B2 with particle diameters of <4.0 mm (0.98% of the maize employed) and, by sifting, into a fraction of light constituents (0.13%, discarded). The fraction destined for milling, B1, was freed from stories on a stone sorter, in which process a very small stone fraction was separated off.

Therefore, a total of 98.7% of the material, based on the crude maize employed, were used for milling.

To improve the milling, the moisture of the maize was then adjusted to approximately 15% by weight by adding water. The maize was then left for approximately 8 hours before further processing.

a.2. Fractionating Milling
Variant 1: Degermination on a Maize Degerminator

In this process variant, fraction C (>6.5 mm) of the precleaned maize was passed to a maize degerminator. The maize degerminator used was a device which comprised a drawing-in worm and a processing zone, comprising a roller-type rotor and a structured screen which surrounds the roller-type rotor like a jacket. The maize to be processed was conveyed into the processing zone by means of the drawing-in worm. Degermination was achieved by the intensive processing between the roller-type rotor and the screen, and by a suitable adjustment of the impact pressure at the mouth. The germs were separated from the seed coat and the endosperm fraction in this process. After passing through the degerminator, the fractions obtained are separated by sifting and screening. The so-called peeled-off flour was separated off as the smallest fraction by screening. The seed coats (bran fraction) which had been freed were separated off by sifting. Since the separation of endosperm, seed coat and germ within the maize degerminator was incomplete, the fraction which had not been separated off by screening and sifting was passed to a three-step roller-mill pass. The maize fraction B1 which had been obtained in the precleaning step (particle diameter between 6.5-4 mm) was also passed directly to the multi-step roller-mill pass. When passing through the roller mill, the particles added were comminuted, upon passing, by two rollers which rotated at different speeds. After each pass, the seed coats and germs which had been liberated were separated by screening and sifting from a sufficiently comminuted endosperm fraction and from an endosperm fraction which may still have had germ and seed coat constituents attached to it. For the further separation of germ and seed coat constituents, this endosperm fraction was passed through the next roller-mill pass.

By combining the endosperm fractions (84% by weight of the maize employed for milling), a meal with a starch content of 84.4% by weight and a fat content of 1.28% by weight was obtained. The resulting germ fraction (12.3% by weight of the maize employed) had a starch content of 24.1% by weight and a fat content of 20.8% by weight. The seed coat fraction (3.6% by weight of the maize employed) had a starch content of 24.4% by weight and a fat content of 1.9% by weight.

Variant 2: Degermination on Roller Mills

In a further process variant, the fractions C (>6.5 mm) and B1 (6.5 to 4.0 mm) of the precleaned maize are passed directly to a roller mill with two pairs of rollers with in each case two rollers which rotate in opposite directions at different speeds. In this roller mill, the maize kernels were comminuted by two rollers which rotated at different speeds, and the seed coats, the endosperm and the maize germs were partially separated by shear forces. After this first disruption, three further passes through roller mills followed, during which the added particles were, again, comminuted when passing through two rollers which rotated at different speeds. After each pass, the seed coats and germs which had been liberated were separated by screening and sifting from a sufficiently comminuted endosperm fraction and from an endosperm fraction which may still have had germ and seed coat constituents attached to it. For the further separation of germ and seed coat constituents, this endosperm fraction was passed through the next roller-mill pass.

By combining the endosperm fractions (85.3% by weight of the maize employed for milling), a meal with a starch content of 84.6% by weight and a fat content of 1.74% by weight was obtained. The resulting germ fraction (11% by weight of the maize employed) had a starch content of 25.5% by weight and a fat content of 19.0% by weight. The seed coat fraction (=bran fraction, 3.7% by weight of the maize employed) had a starch content of 24.3% by weight and a fat content of 2.7% by weight.

a.3. Size Reduction

To reduce the size, each of the three fractions obtained (endosperm, germ and seed coat) were milled separately.

Milling of the endosperm fraction was performed in a roller mill. This gave a wheat flour with the following size distribution.

| | Particle size [μm] | | | | | |
|---|---|---|---|---|---|---|
| | >905 | >410 | >310 | >200 | >132 | <132 | Total |
| Percent by weight [%] | 0.1 | 1.9 | 11.6 | 41.3 | 23.5 | 21.6 | 100.0 |

The germ fraction was ground in a hammer mill with a screen diameter of 3 mm. Milling gave the following size distribution:

| | Particle size [μm] | | | | |
|---|---|---|---|---|---|
| | >2300 | >1610 | >1200 | >700 | <700 | Total |
| Percent by weight [%] | 0.10 | 1.20 | 4.99 | 27.42 | 66.30 | 100.0 |

Milling of the seed coat fraction was likewise performed in a hammer mill with a screen diameter of 3 mm. This gave the following size distribution:

| | Particle size [μm] | | | | |
|---|---|---|---|---|---|
| | >2300 | >1610 | >1200 | >700 | <700 | Total |
| Percent by weight [%] | 0.00 | 0.20 | 1.80 | 24.65 | 73.35 | 100.00 |

Step b): Enzymatic Liquefaction and Saccharification of Maize Meal

General Protocol b1:

To carry out the experiments, a combination of continuously and batchwise operated reactors was employed. First, the maize meal was slurried. To this end, water and maize meal were introduced into two stirred tanks of in each case 250 l and the mixture was heated at 60° C., using direct steam. Depending on the chosen amount of maize meal, $CaCl_2$ (0.006% by weight based on the amount of meal employed (dry matter)) was then added. In the next step, the pH was brought to 5.5-5.8 using 10% by weight sulfuric acid, and α-amylase (Liquozyme Supra, Novozyme A/S, 0.04% based on the amount of meal employed (DM)) was added. The slurry thus prepared was pumped, by means of an eccentric screw pump, through a jet cooker (Hydroheater M101, Hydro-Thermal Corp.), in which the slurry was heated at 109° C. by means of direct steam. The starch present in the maize meal was thereby gelatinized, and the α-amylase employed resulted in the cleavage of the starch molecules. The stream leaving the jet cooker was passed into a tubular reactor with a temperature of 109° C., with a residence time of 5 min. The reaction mixture leaving the tubular reactor was released to ambient pressure into a 30-l tank, whereby temperatures of 95-99° C. were established. Under these conditions, the reaction mixture was then pumped into a second tubular reactor with a residence time of 120 min. The liquefied mixture was then pumped from this second tubular reactor either into a 250-l or into a 2000-l stirred tank, as desired.

An enzymatic cleavage of the dextrins, which had formed by the liquefaction as the result of the cleavage of the starch molecules, to give glucose was carried out in the stirred tanks, in each case batchwise. To this end, a first step consisted of lowering the temperature of the liquefied mixture to 63° C., adjusting the pH to 4.3 (±0.1) with 10% strength sulfuric acid and then adding glucoamylase (Dextrozyme DX 1.5×, Novozyme A/S, 0.06% based on the amount of meal employed (DM)). After addition of the glucoamylase, the reaction mixture was then held for 48 hours at 63-65° C., and then the cleavage of the dextrins to give glucose was stopped by denaturing the glucoamylase by raising the temperature to >70° C.

Various maize meals generated analogously to step a) were liquefied and saccharified. These meals had the following compositions:

| | Residual moisture [%] | Starch* [%] | Crude protein* [%] | Crude fat* [%] | Crude ash* [%] | Crude fiber* [%] |
|---|---|---|---|---|---|---|
| Meal 1 | 9.32 | 83.2 | 8.3 | 1.7 | 0.7 | 1.4 |
| Meal 2 | 9.44 | 83.1 | 7.7 | 1.5 | 0.6 | 1.3 |
| Meal 3 | 11.46 | 85.8 | 7.6 | 1.7 | 0.3 | 0.7 |

*Percent by weight based on dry-matter content

The meals had the following particle size distribution:

| Percent by weight* | Particle size [μm] | | | | | |
|---|---|---|---|---|---|---|
| | >850 | >600 | >425 | >300 | >250 | <250 |
| Meal 1 | — | — | 2 | 30 | 10 | 58 |
| Meal 2 | — | — | 2 | 50 | 6 | 42 |
| Meal 3 | — | — | 2 | 22 | 11 | 64 |

*Percent by weight based on dry-matter content

All meals were slurried and liquefied as described in general protocol b1), the ratio between meal and water being selected in each case in such a way that a starch content of 31.0% by weight resulted in each case upon liquefaction and saccharification. According to the different starch contents of the individual meals, therefore, dry-matter contents of 37.3% by weight (meal 1, meal 2) and 36.1% by weight (meal 3) were employed for the liquefaction and saccharification. After 48 h, this procedure gave a sugar solution (crude glucose) with sugars of different chain length. The crude glucoses thus obtained had a glucose concentration (DP1) of 29.1-29.6% by weight. The percentages of glucose (DP1) and of oligoglucoses (DP2 to DP4) in the crude glucoses obtained are compiled in the table which follows:

| Degree of polymerization | Meal 1 | Meal 2 | Meal 3 |
|---|---|---|---|
| DP 1 [%] | 945 | 94.7 | 95.5 |
| DP 2 [%] | 2.9 | 2.9 | 2.6 |
| DP 3 [%] | 1.5 | 1.5 | 1.0 |
| DP 4 [%] | 0.9 | 0.7 | 0.8 |
| > DP 4 [%] | 0.3 | 0.2 | 0.2 |

In a further experiment, meal 1, which had a starch content of 34.7% by weight, was employed for the liquefaction and saccharification. This gave a dry-matter content of 41.7% by weight in the slurry. In this experiment, the amount of glucoamylase was reduced to 0.06% (based on the amount of meal employed (DM)). After 48 h, this procedure gave a crude glucose with a glucose concentration of 32.7% by weight. 94.2% of the sugars generated had a degree of polymerization of 1.

General Protocol b2:

As an alternative to the batchwise slurrying of the maize meal in stirred tanks, which had been described under b1), the meal was slurried in a continuously operating mixer (CoriMix K-TT, Lödige-Drais). To this end, a total of 693 l of water were warmed to a temperature of 58.1° C. in the stirred tank intended for the saccharification process, which had a volume of 2500 l, and 69 g of Ca(OH)$_2$ and 106 g of Liquozyme were added. The maize meal which was admixed (11.4% by weight of residual moisture) had a temperature of 31° C. In a first point of operation, 109.2 kg/h of the water were run to 82.8 kg/h of maize meal, which generated a total of 192 kg/h of a homogeneous maize meal suspension with a starch content of 33.9% by weight and a dry-matter content of 38.2% by weight. The temperature of the mixture was 42° C. in a second point of operation, the fed amounts of both water and meal were increased. In the mixer, a homogeneous maize meal suspension of in total 475.8 kg/h with a starch content of 35.8% by weight and a dry-matter content of 40.5% by weight was generated from 217.6 kg/h of maize meal and 258.2 kg/h of water. The temperature at the second point of operation was also 42° C.

The maize meal suspension thus obtained was liquefied in an arrangement of jet cooker and two sequentially connected tubular reactors analogously to the manner described in general protocol b1 and subsequently saccharified batchwise.

Step c): Removal of the Nonhydrolyzed Solids from the Crude Glucose (Maize Gluten and, if Appropriate, Bran Constituents)

The separation of the nonhydrolyzed solids from the crude glucose obtained in step b) was carried out in a decanter (type Z23-4/401 s, Flottweg). Scheme 1 hereinbelow gives an overview over the individual process steps.

Scheme 1:

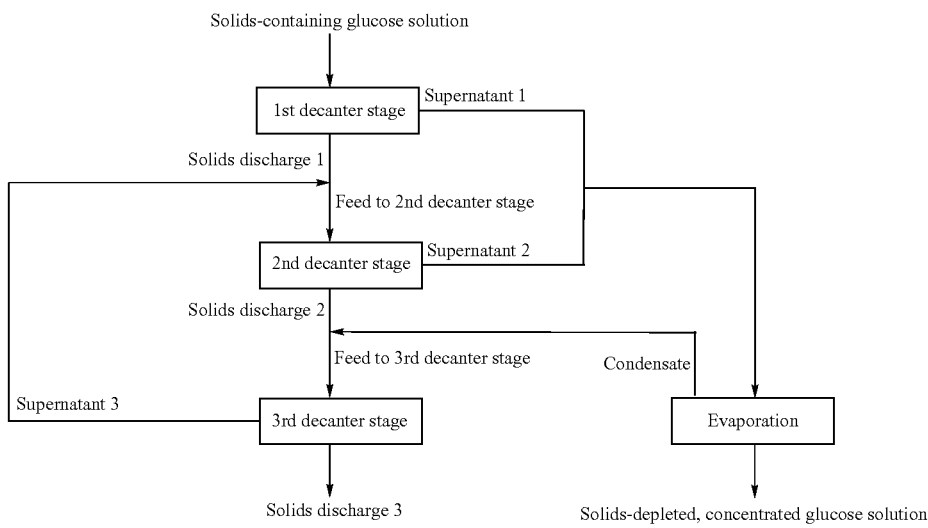

A glucose solution which comprised a total dry-matter content of 36.1% by weight, with a glucose content of 28.6% by weight and a disaccharide content of 0.8% by weight, was prepared from meal 2 by the process described in step b). The specific gravity of the glucose solution was 1.15 g/cm$^3$.

In accordance with scheme 1, 440 kg of this solids-containing glucose solution was conveyed to the first decanter stage at a flow rate of 440 kg/h and separated into two fractions (supernatant 1 and solids discharge 1). In this manner, 326 kg of supernatant (supernatant 1) with a glucose content of 30.3% by weight and a disaccharide content of 0.9% by weight, a total dry-matter content of 33.1% by weight and a supernatant gravity of 1.15 g/cm$^3$ were obtained. The solids discharge from the first decanter stage (solids discharge 1) of 114 kg had a glucose content of 23.6% by weight and a disaccharide content of 0.6% by weight. The total dry-matter content of solids discharge 1 was 44.6% by weight.

In the next step, solids discharge 1 was resuspended together with 154 kg of the supernatant of the third decanter stage (supernatant 3), which gave 268 kg of a solids-containing glucose solution with a glucose content of 11.9% by weight and a disaccharide content of 0.4% by weight. The total dry-matter content of this solution was 23.2% by weight. This solids-containing glucose solution was then conveyed to the second decanter stage at a flow rate of 470 kg/h and again separated into two fractions (supernatant 2 and solids discharge 2). In this manner, 169 kg of supernatant 2 with a glucose content of 13.2% by weight, a disaccharide content of 0.4% by weight, a total dry-matter content of 14.1% by weight and a gravity of 1.07 g/cm$^3$ were obtained. Solids discharge 2 was generated in an amount of 99 kg and had a glucose content of 9.2% by weight and a disaccharide content of 0.2% by weight. The total dry-matter content of solids discharge 2 was 38.6% by weight.

In the next step, solids discharge 2 was then resuspended together with 154 kg of condensate from the glucose evaporation, giving 253 kg of a solids-containing glucose solution with a glucose content of 3.8% by weight and a disaccharide content of 0.2% by weight. The total dry-matter content of this solution was 16.1% by weight. This solids-containing glucose solution was then conveyed to the third decanter stage at a flow rate of 670 kg/h and again separated into two fractions (supernatant 3 and solids discharge 3). 144 kg of supernatant 3 with a glucose content of 4.5% by weight and a disaccharide content of 0.1% by weight were obtained. At a total dry-matter content of 4.4% by weight, the gravity of supernatant 3 was 1.03 g/cm$^3$. Solids discharge 3 was generated in an amount of 109 kg and had a glucose content of 3.1% by weight and a disaccharide content of 0.1% by weight. The total dry-matter content of this solids discharge 3 was 31.6% by weight.

The supernatant of the first two decanter stages (supernatant 1 and supernatant 2) were combined. In this manner, 494 kg of a solids-depleted glucose with a volumetric solids content of 1.0% by volume, as determined by centrifugation at 1650 g, were obtained. The mixture had a glucose content of 24.4% by weight and a disaccharide content of 0.7% by weight. At a total dry-matter content of 26.6% by weight, the gravity of the mixture was 1.12 g/cm$^3$.

The glucose solution thus produced was evaporated in an 800 l double-walled stirred container. To this end, hot steam with a temperature of 140° C. was applied to the stirred container. The temperature of the glucose solution was held at 95° C. by establishing a slightly reduced pressure.

At the end of the evaporation process, 202 kg of glucose solution remained in the stirred container. This solution had a glucose content of 60.5% by weight and a disaccharide content of 1.6% by weight. The total dry-matter content of the solution was 65.0% by weight. The crude protein content is 1.9% by weight, and the crude fiber and crude ash content 0.01% by weight.

The resulting glucose solution comprised approximately 580 mg/kg of protein or amino acids, with the following amino acid distribution: 119 mg/kg of aspartate, 7 mg/kg of threonine, 15 mg/kg of serine, 55 mg/kg of glutamine, 16 mg/kg of glycine, 64 mg/kg of alanine, 5 mg/kg of cysteine, 15 mg/kg of valine, 3 mg/kg of methionine, 11 mg/kg of isoleucine, 9 mg/kg of leucine, 33 mg/kg of tyrosine, 17 mg/kg of phenylalanine, 5 mg/kg of histidine, 10 mg/kg of lysine, 18 mg/kg of arginine and 190 mg/kg of proline. The pH of the solution was 4.4. The solution comprised 0.12% by weight of $SO_4^{2-}$, 19 mg/kg of $Cl^-$, 0.17% by weight of $K^+$, 0.01% by weight of $Ca^{2+}$, 42 mg/kg of $Na^+$ and 0.12% by weight of $PO_4^{3-}$. The viscosity of the solution was 84 cP at 30° C.

EXAMPLE 2

Production of a Maize Gluten Powder by Drying the Solids Fraction Obtained in Example 1, Step c)

To produce the maize gluten powder, the solid (solids discharge 3) which had been separated off in example 1, step c), was dried in a multicoil pilot dryer (NLI). This dryer, which had a volume of 300 l, featured three rotating heating coils with a total surface of 3 m$^2$. To operate the dryer, the material to be dried was introduced, the pressure in the dryer was subsequently adjusted to 600 mbar, and the dryer was heated by 6 bar steam in the heating coils. In addition, the dryer rotated at 13 revolutions per minute. At the beginning of the experiments, 10 kg of predried material from an earlier solids separation was introduced in order to avoid material caking to the heating coils. After addition of 10 kg of the moist solid with a dry-matter content of 31.6% by weight (solids discharge 3 of step c) of example 1), drying was carried out for 45 min. Then, in each case more moist solid (solids discharge 3 of step c) of example 1) was added at further intervals, dried, and the residual moisture was determined in each case at a later point of the drying process.

| Time [min] | 0 | 45 | 70 | 105 | 120 | 145 | 165 | 200 | 220 | 250 | 290 |
| --- | --- | --- | --- | --- | --- | --- | --- | --- | --- | --- | --- |
| Solid$_{dry}$ [kg] | 10 | — | — | — | — | — | — | — | — | — | — |
| Solid$_{moist}$ [kg] | 10 | 10 | 20 | 6 | 18 | 16 | 18 | 22 | 40 | 40 | — |
| Residual moisture [% by wt] | — | — | — | — | 24.0 | 22.8 | 25.6 | 10.4 | 15.3 | 19.2 | 10.1 |

The dry product produced in this manner had a mean particle size of 369 μm and a bulk density of 531 g/l. The dry product consisted of 36.8% by weight of crude protein, 20.1% by weight of sugars, 7.0% by weight of crude fat and 4.5% by weight of crude fiber.

EXAMPLE 3

Use of the Produced Glucose Solution in a Fermentation

A glucose solution produced as described in example 1 was employed in fermentations with *Corynebacterium glutamicum* for the production of lysine.
3.1 Construction of a Lysine-Overproducing *C. glutamicum* Strain ATCC13032 lysC$^{fbr}$
3.1.1 Construction of Plasmid pCIS lysC In the first step of the strain construction, an allelic substitution of the wild-type gene which codes for the enzyme aspartate kinase (lysC) was carried out in *C. glutamicum* ATCC13032. Here, a nucleotide substitution was carried out in the lysC gene so that, in the resulting protein, the amino acid Thr at position 311 was replaced by Ile. Starting from the chromosomal DNA from ATCC13032 as template for a PCR reaction, lysC was amplified with the oligonucleotide primers (SEQ ID NO: 1)
5'-GAGAGAGAGACGCGTCCCAGTGGCTGAGACGCATC-3'
and (SEQ ID NO: 2)
5'-CTCTCTCTGTCGACGAATTCAATCTTACGGCCTG-3' with the aid of the Pfu-Turbo PCR system (Stratagene, USA), following the manufacturer's instructions. Chromosomal DNA from *C. glutamicum* ATCC13032 was prepared by the method of Tauch et al. (1995) Plasmid 33:168-179 or Eikmanns et al. (1994) Microbiology 140:1817-1828. The amplified fragment is flanked at its 5' end by a SalI restriction cleavage site and at its 3' end by a MluI restriction cleavage site. Prior to cloning, the amplified fragment was digested with these two restriction enzymes and purified with GFX™ PCR, DNA and Gel Band Purification Kit (Amersham Pharmacia, Freiburg).

The resulting polynucleotide was cloned via the SalI and MluI restriction cleavages into pCLIK5 MCS integrativ SacB, hereinbelow referred to as pCIS (SEQ ID NO:3) and transformed into *E. coli* XL-1 blue. A selection for plasmid-harboring cells was achieved by plating on kanamycin (20 μg/ml)-comprising LB agar (Lennox, 1955, Virology, 1:190). The plasmid was isolated and the expected nucleotide sequence was verified by sequencing. The preparation of the plasmid DNA was carried out using methods and materials from Qiagen. Sequencing reactions were carried out by the method of Sanger et al. (1977) Proceedings of the National Academy of Sciences USA 74:5463-5467. The sequencing reactions were separated and evaluated by means of ABI Prism 377 (PE Applied Biosystems, Weiterstadt). The resulting plasmid was referred to as pCIS lysC (SEQ ID NO:4). It comprises the following essential portions:

| Position | Sequence type | Description |
| --- | --- | --- |
| 155-1420 | CDS | lysC |
| Complement (3935 ... 5356) | CDS | sacB/*Bacillus subtilis* |
| Complement (5357 ... 5819) | promoter | promoter/sacB |
| Complement (3913 ... 3934) | C region | sacB/downstream region |
| 1974 ... 2765 | CDS | kanamycin resistance |
| Complement (3032 ... 3892) | CDS | replication origin/ *E. coli*/plasmid pMB |

3.1.2 Mutagenesis of the *C. glutamicum* lysC Gene

The directed mutagenesis of the *C. glutamicum* lysC gene was carried out using the QuickChange Kit (Stratagene, USA) following the manufacturer's instructions. The mutagenesis was carried out in the plasmid pCIS lysC (SEQ ID NO:4). The following oligonucleotide primers were synthesized for the substitution of thr 311 by 311 ile with the aid of the Quickchange method (Stratagene):

(SEQ ID NO: 5)
5'-CGGCACCACCGACATCATCTTCACCTGCCCTCGTTCCG-3'

(SEQ ID NO: 6)
5'-CGGAACGAGGGCAGGTGAAGATGATGTCGGTGGTGCCG-3'

The use of these oligonucleotide primers in the Quickchange reaction leads, in the lysC gene (SEQ ID NO:7), to a substitution of the nucleotide in position 932 (of C by T). The resulting amino acid substitution Thr311Ile in the lysC gene was verified by a sequencing reaction after transformation into *E. coli* XL1-blue and plasmid preparation. The plasmid was named pCIS lysC thr311ile (SEQ ID NO:8). It comprises the following essential portions:

| Position | Sequence type | Description |
| --- | --- | --- |
| 155-1420 | CDS | LysC (thr311ile) |
| Complement (3935 ... 5356) | CDS | sacB\*Bacillus subtilis* |
| Complement (5357 ... 5819) | promoter | promoter\sacB |
| Complement (3913 ... 3934) | C region | sacB\downstream region |
| 1974 ... 2765 | CDS | kanamycin resistance |
| Complement (3032 ... 3892) | CDS | replication origin\*E. coli*\plasmid pMB |

3.1.3 Transformation of pCIS lysC thr311ile into *C. glutamicum* (Strain ATCC13032)

The plasmid pCIS lysC thr311ile was transformed into *C. glutamicum* ATCC13032 by means of electroporation as described by Liebl et al., FEMS Microbiology Letters 53:299-303 (1989). Modifications of the protocol are described in DE 10046870. The chromosomal arrangement of the lysC locus of individual transformants was verified using standard methods by means of Southern blot and hybridization as described in Sambrook et al., Molecular Cloning. A Laboratory Manual, Cold Spring Harbor (1989). It was thereby ensured that the transformants were those which have the transformed plasmid integrated at the lysC locus by homologous recombination. After such colonies have been grown overnight in media without antibiotic, the cells are plated onto a sucrose CM agar medium (10% sucrose) and incubated for 24 hours at 30° C.

Since the sacB gene comprising in the vector pCIS lysC thr311ile converts sucrose into a toxic product, only those colonies which have the sacB gene deleted by a second homologous recombination step between the wild-type gene lysC and the mutated gene lysC thr311ile are capable of growing. During the homologous recombination, either the wild-type gene or the mutated gene can be deleted together with the sacB gene. When the sacB gene is removed together with the wild-type gene, a mutated transformant results.

Growing colonies were picked out and studied for a kanamycin-sensitive phenotype. Clones with deleted sacB gene must simultaneously demonstrate kanamycin-sensitive growth behavior. Such kanamycin-sensitive clones were studied for their lysine productivity in a shake flask. For comparison, the untreated *C. glutamicum* ATCC13032 was grown. Clones whose lysine production was increased over the control were selected, chromsomal DNA was obtained, and the corresponding region of the lysC gene was amplified by a PCR reaction (Pfu-Turbo PCR Systems; Stratagene, USA) following the manufacturer's instructions and sequenced (by the method of Sanger et al., loc. cit.). Such a clone with the characteristic of enhanced lysine synthesis and confirmed mutation in lysC at position 932 was referred to as ATCC13032 lysC$^{fbr}$.

3.2 Preparation of the Fermentation Media
3.2.1 Preculture 1:

Preculture 1 was carried out in a 5 l fermenter. The working volume in the fermenter was 3 l. The composition of the preculture medium is shown in the table which follows.

| Media component | Concentration |
| --- | --- |
| Sucrose | 4.75% |
| Ammonium sulfate | 1.00% |
| MgSO$_4$ | 0.05% |
| KH$_2$PO$_4$ | 0.20% |
| Urea | 0.25% |
| Corn steep liquor | 5.00% |
| Hydrolyzed soya protein | 4.00% |
| Nicotinic acid | 4.95 mg/l |
| Thiamine* HCl | 1 mg/l |
| d-Biotin | 1.5 mg/l |
| β-Alanine | 10 mg/l |
| FeSO$_4$ | 10 mg/l |
| MnSO$_4$ | 10 mg/l |
| CuSO$_4$ | 1 mg/l |
| Antifoam | 0.1 g/l |

The sugar was dissolved in water directly in the fermenter and sterilized in situ. The nitrogen sources were sterilized separately from the sugars and then added. The vitamin and microsalt solution was also prepared separately and added to the fermenter after the sterilization, through a 0.2 μm sterile filter. After addition of all media components, the pH is brought to 7 by means of NaOH.

3.2.2 Preculture 2

Preculture 2 was carried out in a 50 l fermenter. The working volume in the fermenter was 30 l. The composition of the second preculture medium is shown in the table which follows.

| Media component | Concentration |
| --- | --- |
| Low-quality molasses | 3.50% |
| Sucrose | 3.50% |
| Corn steep liquor | 3.63% |
| Ammonium sulfate | 0.70% |
| Urea | 0.25% |
| H$_3$PO$_4$ | 0.25% |
| Nicotinic acid | 7 mg/l |
| Thiamine* HCl | 2.5 mg/l |
| d-Biotin | 0.05 mg/l |
| β-Alanine | 5 mg/l |
| MnSO$_4$ | 7 mg/l |
| CuSO$_4$ | 1.5 mg/l |
| Antifoam | 0.25 g/l |
| Betaine 97% | 0.07% |

As in the case of preculture medium 1, the sugar sources were dissolved in water directly in the fermenter and sterilized in situ. The nitrogen sources were sterilized separately from the sugars and then added. The vitamin and microsalt solution was also prepared separately and added to the fermenter after the sterilization, through a 0.2 μm sterile filter. After addition of all media components, the pH is brought to 7 by means of NaOH.

3.2.3 Main Culture:

The main culture was run as a fed-batch process, so that, besides the starting medium, a feed medium was also employed. A fermenter with a nominal volume of 300 l, the maximum working volume being 190 l, was employed.

At the beginning of each main fermentation, 110 l of the starting medium described in the table hereinbelow were placed into the fermenter. Again, the sugar source was introduced into the fermenter together with water and sterilized in situ. The nitrogen sources were sterilized separately from the sugars. The vitamin and microsalt solution was also prepared separately and added to the fermenter after the sterilization, through a 0.2 μm sterile filter. After addition of all media components, the pH is brought to 7 by means of NaOH.

| Media component | Concentration |
| --- | --- |
| Low-quality molasses | 3.00% |
| Corn steep liquor | 1.49% |
| Ammonium sulfate | 5.00% |
| Antifoam | 0.1 g/l |
| Betaine 97% | 0.07% |
| H$_3$PO$_4$ | 0.063% |
| Nicotinic acid | 2.5 mg/l |
| Thiamine* HCl | 2.5 mg/l |
| d-Biotin | 0.3 mg/l |
| MnSO$_4$ | 1 mg/l |

The composition in the feed medium is shown in the table hereinbelow. The glucose employed was produced by the process described in example 1. The tank for the feed medium, which was sterilized while empty, was charged stepwise with the separately made vitamin, salt and ammonium sulfate solutions, using a spiral heat exchanger (140° C., residence time 90 s). In a second step, the sugar solutions, also sterilized, were then fed via the heat exchanger.

| Media component | Concentration |
| --- | --- |
| Low-quality molasses | 3.10% |
| Glucose* | 41.90% |
| Ammonium sulfate | 5.50% |
| Antifoam | 1.0 g/l |
| Betaine 97% | 0.07% |
| H$_3$PO$_4$ | 0.05% |
| Nicotinic acid | 0.00045% |
| Thiamine* HCl | 0.000038% |
| d-Biotin | 0.000125% |

*from glucose solution according to example 4

3.3 Fermentation

The preparation of the inoculum for preculture 1 was carried out in 2-l shake flasks with a working volume of 300 ml (preculture medium 1). Starting from slant-agar tubes, the shake flasks were inoculated and shaken for 19 to 24 h at 29° C. and 120 revolutions per minute at a volume-based biomass content of 3% by volume.

The fermenter for preculture 1, which had been prepared as described in section 3.2.1, was inoculated with a shake flask and fermented over 24 h at 30° C., a specific mechanical power input of 5 kW/m$^3$ and 1 vvm aeration. The switch-off criterion for the fermentation was a biomass content of 3% by volume.

Thereafter, the fermenter for preculture 2, which had been prepared as described in section 3.2.2, was inoculated with preculture 1. A suitable amount of preculture 1 was added in order to obtain a volume-based biomass quantity of 0.5% by volume at the beginning. The fermentation was operated at 30° C., 0.7 vvm aeration and a mechanical power input of 2 kW/m$^3$. pH control was effected by gaseous ammonia in the range from 6.8 to 7.0. The usual fermentation time until the switch-off criterion of a volume-based amount of 10% by volume was reached was 14 to 18 h.

In the next step, the main fermenter, which had been prepared as described in section 3.2.3 with the starting medium, was inoculated by pumping all of the contents of preculture 2 into the main fermenter. The main fermentation was carried out at 33° C., 0.5 vvm aeration and a specific mechanical power input of 0.5 kW/m$^3$. During the fermentation, the pH was regulated by means of gaseous ammonia to obtain a pH of from 6.8 to 7.0. At in each case two-hourly intervals, in each case one portion of prepared feed medium was added, the added amount depending on the actual sugar consumption. In order to avoid an accumulation or depletion of sugar, such an amount of sugar was added in each case as is expected to be consumed in the interval to come. As soon as the volume of the contents in the fermenter had exceeded a value of 210 ml, a portion was removed from the fermenter in order to avoid running over. After 48 h, the fermentation was ended and the fermenter was emptied. The portions removed during the fermentation were combined with the fermenter content at the end of the fermentation and worked up together.

Using the *Corynebacterium glutamicum* strain mentioned in section 3.1, the main fermentation generated a total of 21.6 kg of lysine, the procedure having been as described. The lysine concentration at the end of the fermentation was 98 g/l. The biomass content in the 293 kg of produced fermentation liquor was 38 g/l.

3.4 Processing the Fermentation Liquor by Removal and Drying of the Biomass

To remove the biomass, the biomass-comprising fermentation liquor was passed over a decanter CA 225 (Westfalia) at 300 l/h. In total, this procedure gave 48.3 kg of a biomass-comprising fraction with 23% by weight of dry biomass and 244.7 kg of a biomass-free supernatant. A portion of the biomass-comprising fraction was removed and dried on metal trays in a drying oven at 90° C. The residual moisture of the dried biomass was 5.2% by weight. Based on dry matter, the biomass consisted of 62% by weight of crude protein, 0.3% by weight of crude fiber, 5.6% by weight of crude fat, 5.9% by weight of sugars and 3.2% by weight of crude ash.

EXAMPLE 4

Production and Examination of a Feed Composition for Piglets, Using Gluten of Example 2

Samples of the germ fraction obtained in example 1 (sample number n=1), samples of the dried gluten obtained in example 2 (sample number n=2) and samples of the biomass generated in example 3 (sample number n=16) were examined with regard to their composition and their solids characteristics. The sample analysis revealed the composition shown in the table hereinbelow. The mean particle size of the gluten in the test samples was 270 of the biomass between 400 and 500 μm, and of the milling germ fraction between 872 and 1194 μm.

| Parameter | Germ | Gluten | Biomass |
|---|---|---|---|
| Residual moisture [%] | 9.65 | 5.90 | 7.24 |
| Crude protein [%]* | 18.82 | 32.74 | 67.30 |
| Total sugars [%]* | 18.09 | 27.80 | 5.62 |
| Lysine [%]* | 0.00 | 0.03 | 9.09 |
| Crude fiber [%]* | 5.90 | 6.25 | 0.11 |
| Crude fat [%]* | 19.73 | 2.60 | 6.94 |
| Crude ash [%]* | 2.35 | 0.83 | 2.75 |
| Ammonium N [%]* | 0.18 | 0.38 | 0.53 |
| Total N [%]* | 3.01 | 5.24 | 10.77 |
| Sulfate [%]* | 0.09 | 0.13 | 4.71 |
| NDF# [%]* | 26.77 | 34.13 | 11.77 |

*based on dry matter
non-digestible fiber

To produce a feed composition, the individual components were mixed in the ratio 21% biomass:22% germ fraction:57% gluten, in order to obtain a feed composition of the following composition. A total of 16 samples were prepared. On average, the resulting feed composition had a bulk density of between 550 and 700 g/l with a mean particle size of 590 μm.

| Parameter | Feed composition |
|---|---|
| Residual moisture [%] | 9.32 |
| Crude protein [%]* | 36.98 |
| Total sugars [%]* | 27.05 |
| Lysine [%]* | 2.65 |
| Crude fiber [%]* | 4.72 |
| Crude fat [%]* | 10.13 |
| Crude ash [%]* | 2.67 |
| Ammonium N [%]* | 0.30 |
| Total N [%]* | 5.90 |
| Sulfate [%]* | 1.26 |
| NDF# [%]* | 27.66 |

*based on dry matter
non-digestible fiber

The feed composition thus obtained had a high protein content, specifically a high lysine content, and, due to the high fat and sugar content, a high energy content.

In feeding experiments with piglets, the feed preparations thus prepared were tested for their suitability as feed or as feed additives. Starting from a maize/soya diet, 5% of the feed composition obtained were added. The added amount was compensated for by reducing soya meal (73%), maize (20%) and soya oil (7%) to match the composition of the feed mixture. Thus, rations with the same energy and nutrient content were composed by further adaptations in free amino acids and minerals. Finally, the rations were pelleted. The ration comprising the feed mixture was fed to in each case 12 pens with 4-6 week old piglets, with the maize/soya diet acting as comparison. The piglets showed an average weight gain of 261 g/day, a feed consumption rate of 471 g/day and a feed conversion rate of 1.87 kg feed per kg weight gain. Comparable results were obtained when feeding a conventional maize/soya diet, which had been fortified with amino acids in order to generate the desired nutrient content.

The examples show that the feed composition according to the invention can be used instead of, or together with, traditional rations without adverse effects on the feed quality. Rather, the addition of amino acids can be dispensed with. As opposed to the solids generated in the production of bioethanol, the feeds according to the invention are therefore suitable as high-quality replacement for maize and soya in rations for monogastric animals.

EXAMPLE 5

Production of Feed Compositions for Chicken Chicks Using Gluten Obtainable in Analogy to Example 2

Samples of the fractions biomass, gluten and germ produced in accordance with the above examples 1 to 3 were analyzed for their composition. The reference used was soya meal.

A feed composition was prepared by mixing biomass, gluten and germ in the ratio 26:47:27 and analyzed for some main constituents, analogously to example 4. The composition of the further constituents was calculated numerically from the composition of the individual components of this mixture. According to this procedure, the following compositions of the various samples resulted:

| Parameter | Germ | Gluten | Biomass | FC[5] | Soya meal |
|---|---|---|---|---|---|
| Dry-matter content [g/kg] | 912 | 966 | 931 | 937 | 911 |
| Crude ash [g/kg] | 56 | 7 | 28 | —[3] | 65 |
| Crude protein [g/kg] | 160 | 292 | 642 | 349 | 452 |
| Other extracts [g/kg] | 226 | 66 | 85 | 111 | 25 |
| Starch [g/kg] | 200 | 19 | <6 | 63[4] | 53 |
| Sugars [g/kg] | 98 | 384 | 11 | 209[4] | 89 |
| Crude fiber [g/kg] | 53 | 37 | 4 | 32[4] | 69 |
| Energy content ME [MJ/kg][2] | 14.8 | 12.1 | 13.0 | 13.0[4] | 9.9 |
| Ca [g/kg] | <0.5 | <0.5 | <0.5 | <0.5[4] | —[3] |
| P [g/kg] | 2 | 2 | 4.4 | 2.6[4] | —[3] |
| Na [g/kg] | 0.3 | 0.3 | 3.2 | 1.1[4] | —[3] |
| K [g/kg] | 1.2 | 1.2 | 6.1 | 2.5[4] | —[3] |
| Cl [g/kg] | <0.6 | <0.6 | 1.9 | 0.9[4] | —[3] |

[1] According to amino acid analysis
[2] Estimated by regression formula according to the results of the analysis
[3] Not analyzed
[4] Calculated from the individual components of the feed formulation
[5] Feed composition To produce a feed, a basic ration in the following composition was prepared: The composition of the basic ration is shown in the table hereinbelow:

| Component | [g/kg] |
|---|---|
| Maize | 677.1 |
| High-protein soya meal | 211.0 |
| L-Lysine HCl | 7.8 |
| D,L-Methionine | 5.4 |
| L-Threonine | 3.5 |
| L-Tryptophan | 0.9 |
| L-Arginine | 3.8 |
| L-Isoleucine | 3.1 |
| L-Leucine | 0.9 |
| L-Valine | 2.9 |
| L-Phenylalanine | 0.9 |
| L-Cystine | 1.7 |
| Soya oil | 27.5 |
| Monocalcium phosphate | 220.6 |
| Calcium carbonate | 19.1 |
| Sodium chloride | 5.4 |
| Vitamin premix | 5.5 |
| Choline chloride (50%) | 1.4 |
| Trace element premix | 1.4 |

In the feed experiments described hereinbelow, the basic ration was employed as comparison, and three further feeds were employed in which 35% by weight of the ration were replaced by gluten of example 2, by the feed composition, or by soya meal (comparison).

| No. | Composition | |
|---|---|---|
| C1 | Basic ration | 100% |
| 2 | Basic ration + gluten | 65% + 35% |
| 3 | Basic ration + feed composition | 65% + 35% |
| C4 | Basic ration + soya meal | 65% + 35% |

C: Comparison not according to the invention

To ensure homogeneity, a joint basic mixture of this basic ration was generated. Then, the relevant samples were in each case admixed to this basic mixture. Thereafter, the mixtures were compacted through a 3-mm die to give pellets.

To prepare for the feeding experiments, one-day old cockerel chicks (Ross 308) which were kept under floor-management conditions were raised using a commercially available starter ration. On day 8, some of these chicks were removed for the feeding experiments and transferred.

To carry out feeding experiments, in each case 6 parallel experiments with in each case 8 caged chicks were carried out per sample. Up to day 13, these chicks were fed the commercial starter ration. On day 13, the chicks were weighed, and fed the experimental ration over 9 days before being reweighed. In this procedure, the following daily weight gains, feed consumption and feed conversion rates (weight gain/feed consumption, expressed as weight) were found:

| | Feed No. | | | |
|---|---|---|---|---|
| | C1 | 2 | 3 | C4 |
| Weight gain [g/day] | 57.5 | 52.0 | 39.9 | 61.5 |
| Feed consumption [g/day] | 85.5 | 85.1 | 76.5 | 87.8 |
| Feed conversion rate[1] | 1.49 | 1.64 | 1.92 | 1.43 |

[1] g weight gain/g feed consumption

The rations with the gluten according to the invention and the feed compositions according to the invention led to improved feed conversion.

We claim:

1. A process for the production of an aqueous glucose solution from maize, comprising:
   a) fractionating dry milling of maize kernels, where the maize kernels are separated into a maize-starch-comprising endosperm fraction and a high-oil germ fraction and optionally a bran fraction;
   b) enzymatical liquefaction and saccharification of the maize starch in an aqueous suspension of the endosperm fraction, which gives an aqueous glucose solution comprising maize gluten; and
   c) depletion of the maize gluten and optionally any bran present from the aqueous glucose solution;
   where in step b) an aqueous suspension of the maize flour obtained in step a) and containing the endosperm fraction and optionally the bran fraction is employed, where the amount of maize flour is chosen in such a way that the aqueous suspension comprises from 30 to 45% by weight of starch, based on the total weight of the suspension.

2. The process according to claim 1, wherein the milling in step a) is carried out in the presence of from 1 to 30% by weight of water, based on the weight of the maize kernels employed.

3. The process according to claim 1, wherein, in step a), essentially only the germ fraction and the bran fraction are separated from the endosperm fraction.

4. The process according to claim 1, wherein, in step a), the bran fraction and the germ fraction are separated from the endosperm fraction and some of the bran fraction is returned to the endosperm fraction.

5. The process according to claim 1, wherein, in step a), the endosperm fraction is milled to a mean particle size in the range of from 0.1 to 1.0 mm.

6. The process according to claim 1, wherein, to carry out the liquefaction, the aqueous suspension of the endosperm fraction is heated to a temperature above the gelatinization temperature of the maize starch.

7. The process according to claim 1, wherein at least 90% of the maize gluten, based on the total gluten constituents present in the glucose solution, are separated from the aqueous glucose solution.

8. The process according to claim 1, wherein the depletion of the maize gluten and bran constituents which may be present is carried out in such a way that the glucose solution comprises less than 10% by volume of solids after the depletion.

* * * * *